United States Patent [19]

Wozney et al.

[11] Patent Number: 5,459,047

[45] Date of Patent: Oct. 17, 1995

[54] BMP-6 PROTEINS

[75] Inventors: John M. Wozney, Hudson; Elizabeth A. Wang, Carlisle; Vicki A. Rosen, Brookline; Anthony J. Celeste, Hudson, all of Mass.

[73] Assignee: Genetics Institute, Inc., Cambridge, Mass.

[21] Appl. No.: 251,069

[22] Filed: May 27, 1994

Related U.S. Application Data

[62] Division of Ser. No. 926,081, Aug. 5, 1992, which is a division of Ser. No. 490,033, Mar. 7, 1990, Pat. No. 5,187,076, which is a continuation-in-part of Ser. No. 370,544, Jun. 23, 1989, which is a continuation-in-part of Ser. No. 347,559, May 4, 1989, abandoned, which is a continuation-in-part of Ser. No. 179,100, Apr. 8, 1988, and Ser. No. 179,101, Apr. 8, 1988, abandoned, and Ser. No. 179,197, Apr. 8, 1988, said Ser. No. 179,100, and Ser. No. 179,101, and Ser. No. 179,197, each, is a continuation-in-part of Ser. No. 28,285, Mar. 20, 1987, abandoned, and Ser. No. 31,346, Mar. 26, 1987, Pat. No. 4,877,864, said Ser. No. 28,285, and Ser. No. 31,346, each, is a continuation-in-part of Ser. No. 943,332, Dec. 17, 1986, abandoned, and Ser. No. 880,776, Jul. 1, 1986, abandoned.

[51] Int. Cl.⁶ ............................. C12P 21/02; C12N 7/00; C12N 5/00; C12N 1/21; C12N 15/00; C07H 15/12; C07K 3/00; A01N 37/18

[52] U.S. Cl. .................. 435/69.1; 435/320.1; 435/235.1; 435/252.3; 435/240.2; 530/300; 530/350; 514/2; 536/23.1

[58] Field of Search ............................. 435/69.1, 320.1, 435/235.1, 252.3, 240.2; 530/300, 350; 514/2; 536/23.1

[56] References Cited

U.S. PATENT DOCUMENTS

| | | | |
|---|---|---|---|
| 4,294,753 | 10/1981 | Urist | 530/395 |
| 4,434,094 | 2/1984 | Seyedin et al. | 530/416 |
| 4,455,256 | 6/1984 | Urist | 530/350 |
| 4,563,350 | 1/1986 | Nathan | 424/95 |
| 4,608,199 | 8/1986 | Caplan et al. | 530/414 |
| 4,627,982 | 12/1986 | Seyedin et al. | 424/95 |
| 4,681,763 | 7/1987 | Nathanson | 424/95 |
| 4,737,578 | 4/1988 | Evans | 530/350 |
| 4,761,471 | 8/1988 | Urist | 530/350 |
| 4,774,228 | 9/1988 | Seyedin | 514/21 |
| 4,774,322 | 9/1988 | Seyedin | 530/353 |
| 4,789,732 | 12/1988 | Urist | 530/350 |
| 4,798,885 | 1/1989 | Mason | 530/350 |
| 4,804,744 | 2/1989 | Sen | 530/350 |
| 4,810,691 | 3/1989 | Seyedin | 514/2 |
| 4,843,063 | 6/1989 | Seyedin | 514/2 |
| 4,886,747 | 12/1989 | Derynk | |
| 4,968,590 | 11/1990 | Kuberasampath et al. | 530/326 |
| 5,011,691 | 4/1991 | Oppermann | 424/423 |
| 5,106,626 | 4/1992 | Parson et al. | |
| 5,108,753 | 4/1992 | Kuberasampath | |
| 5,187,076 | 2/1993 | Wozney et al. | 435/69.1 |

FOREIGN PATENT DOCUMENTS

| | | | |
|---|---|---|---|
| 2017466 | 5/1990 | Canada | C12N 15/16 |
| 336760 | 6/1989 | European Pat. Off. | C07K 7/00 |
| 416578A2 | 5/1990 | European Pat. Off. | C12N 15/00 |
| 409472A1 | 11/1990 | European Pat. Off. | C21N 15/12 |
| WO89/09788 | 10/1989 | WIPO | C07K 13/00 |
| WO89/09787 | 10/1989 | WIPO | C07K 13/00 |
| WO90/03733 | 4/1990 | WIPO | A01N 63/02 |
| WO91/02744 | 3/1991 | WIPO | C07K 15/06 |
| WO91/05802 | 5/1991 | WIPO | C07K 15/00 |
| WO91/18047 | 11/1991 | WIPO | |

OTHER PUBLICATIONS

Urist et al., *Science*, 220:680–686 (1983).
Luyten et al., *The Journal of Biological Chemistry*, 264(23) 13377–13380 (Aug. 15, 1989).
Sampath, et al., *Proc. Natl. Acad. Sci.*, 84:7109–7113 (1987).
Ozkaynak et al., *The EMBO Journal*, vol. 9, No. 7: 2085–2093 (1990).
Wozney et al., *Science*, vol. 242, pp. 1528–1534 (1988).
Maniatis et al., *Molecular Cloning, a Laboratory Manual Cold Spring Harbor Laboratory CSH N.Y. (1982)*, pp. 310–323 & 404–433.
Lyons et al., *Proc. Natl. Acad. Sci.*, (USA), 86:4554–4558 (Jun. 1989).
Hammonds et al., *Molecular Endocrinology*, 5:149–155 (1991).

*Primary Examiner*—Joan Ellis
*Attorney, Agent, or Firm*—Ellen J. Kapinos; Thomas J. DesRosier

[57] ABSTRACT

Purified BMP-6 proteins and processes for producing them are disclosed. The proteins may be used in the treatment of bone and/or cartilage defects and in wound healing and related tissue repair.

14 Claims, 8 Drawing Sheets

FIGURE 1

```
  1  TCTAGAGGTGAGAGCAGCCAACAAGAGAAAAAATCAAAACCGCAATAAATCCGGCTCTCAT   61
     LeuGluValArgAlaAlaAsnLysArgLysAsnGlnAsnArgAsnLysSerGlySerHis
     (1)                                                    (15)

62  CAGGACTCCTCTAGAATGTCCAGTGTTGGAGATTATAACACCAGTGAACAAAAACAAGCC   121
     GlnAspSerSerArgMetSerSerValGlyAspTyrAsnThrSerGluGlnLysGlnAla
                    (23)

122  TGTAAAAAGCATGAACTCTATGTGAGTTTCCGGGATCTGGGATGGCAGGACTGGATTATA   181
     CysLysLysHisGluLeuTyrValSerPheArgAspLeuGlyTrpGlnAspTrpIleIle
                   (42)

182  GCACCAGAAGGATATGCTGCATTTTATTGTGATGGAGAATGTTCTTTTCCACTCAATGCC   241
     AlaProGluGlyTyrAlaAlaPheTyrCysAspGlyGluCysSerPheProLeuAsnAla

242  CATATGAATGCCACCAATCATGCCATAGTTCAGACTCTGGTTCACCTGATGTTCCCTGAC   301
     HisMetAsnAlaThrAsnHisAlaIleValGlnThrLeuValHisLeuMetPheProAsp

302  CACGTACCAAAGCCTTGCTGCGCGACAAACAAACTAAATGCCATCTCTGTGTTGTACTTT   361
     HisValProLysProCysCysAlaThrAsnLysLeuAsnAlaIleSerValLeuTyrPhe

362  GATGACAGCTCCAATGTCATTTTGAAAAAGTACAGAAATATGGTCGTGCGTTCGTGTGGT   421
     AspAspSerSerAsnValIleLeuLysLysTyrArgAsnMetValValArgSerCysGly

422  TGCCACTAATAGTGCATAATAATGGTAATAAGAAAAAAGATCTGTATGGAGGTTTATGA   481
     CysHisEnd
     (140)

481  CTACAATAAAAATATCTTTCGGATAAAGGGGAATTTAATAAAATTAGTCTCGGCTCATT   540

541  TCATCTCTGTAACCCTATGTACAAGAGCATGTATATAGT   578
```

FIGURE 2

```
              9              18              27              36              45
CTG CTG GGC ACG CGT GCT GTG TGG GCC TCA GAG GCG GGC TGG CTG
Leu Leu Gly Thr Arg Ala Val Trp Ala Ser Glu Ala Gly Trp Leu
(1)
              54             63              72              81              90
GAG TTT GAC ATC ACG GCC ACC AGC AAC CTG TGG GTC CTG ACT CCG
Glu Phe Asp Ile Thr Ala Thr Ser Asn Leu Trp Val Leu Thr Pro 99             108            117             126             135
CAG CAC AAC ATG GGG CTG CAG CTG AGC GTG GTC ACG CGT GAT GGG
Gln His Asn MET Gly Leu Gln Leu Ser Val Val Thr Arg Asp Gly 144            153            162             171             180
CTC AGC ATC AGC CCT GGG GCC GCG GGC CTG GTG GGC AGG GAC GGC
Leu Ser Ile Ser Pro Gly Ala Ala Gly Leu Val Gly Arg Asp Gly 189            198            207             216             225
CCC TAC GAC AAG CAG CCC TTC ATG GTG GCC TTC TTC AAG GCC AGT
Pro Tyr Asp Lys Gln Pro Phe MET Val Ala Phe Phe Lys Ala Ser 234            243            252             261             270
GAG GTC CAC GTG CGC AGT GCC CGG TCG GCC CCC GGG CGG CGC CGG
Glu Val His Val Arg Ser Ala Arg Ser Ala Pro Gly Arg Arg Arg 279            288            297             306             315
CAG CAG GCC CGG AAC CGC TCC ACC CCG GCC CAG GAC GTG TCG CGG
Gln Gln Ala Arg Asn Arg Ser Thr Pro Ala Gln Asp Val Ser Arg
                                    (97)

324            333            342             351             360
GCC TCC AGC GCC TCA GAC TAC AAC AGC AGC GAG CTG AAG ACG GCC
Ala Ser Ser Ala Ser Asp Tyr Asn Ser Ser Glu Leu Lys Thr Ala 369            378            387             396             405
TGC CGG AAG CAT GAG CTC TAC GTG AGC TTC CAG GAC CTG GGG TGG
Cys Arg Lys His Glu Leu Tyr Val Ser Phe Gln Asp Leu Gly Trp
(121)       (124)
              414            423            432             441             450
CAG GAC TGG ATC ATT GCC CCC AAG GGC TAC GCT GCC AAC TAC TGT
Gln Asp Trp Ile Ile Ala Pro Lys Gly Tyr Ala Ala Asn Tyr Cys 459            468            477             486             495
GAC GGA GAA TGT TCG TTC CCT CTC AAC GCA CAC ATG AAC GCT ACC
Asp Gly Glu Cys Ser Phe Pro Leu Asn Ala His MET Asn Ala Thr 504            513            522             531             540
AAC CAT GCC ATC GTG CAG ACC CTG GTT CAC CTC ATG AAC CCC GAG
Asn His Ala Ile Val Gln Thr Leu Val His Leu MET Asn Pro Glu 549            558            567             576             585
TAC GTC CCC AAA CCG TGC TGC GCG CCC ACG AAA CTG AAC GCC ATC
Tyr Val Pro Lys Pro Cys Cys Ala Pro Thr Lys Leu Asn Ala Ile 594            603            612             621             630
TCG GTG CTC TAC TTC GAC GAC AAC TCC AAT GTC ATC CTG AAG AAG
Ser Val Leu Tyr Phe Asp Asp Asn Ser Asn Val Ile Leu Lys Lys Tyr Arg Asn
```

FIGURE 2A

```
        639              648              647              666            676
TAC CGG AAC ATG GTC GTA CGA GCG TGT GGG TGC CAC TGACTCGGGG
Tyr Arg Asn MET Val Val Arg Ala Cys Gly Cys His 686              696              706              716            726
TGAGTGGCTG GGGACGCTGT GCACACACTG CCTGGACTCC TGGATCACGT 736              746              756              766            776
CCGCCTTAAG CCCACAGAGG CCCCCGGGAC ACAGGAGGAG ACCCCGAGGC 786              796              806              816            826
CACCTTCGGC TGGCGTTGGC CTTTCGCCC AACGCAGACC CGAAGGGACC 836              846              856              866            876
CTGTCCGCCC CTTGCTCACA CCGTGAGCGT TGTGAGTAGC CATCGGGCTC

886
TAGGAAGCAG CACTCGAG
```

FIGURE 3

```
          10           20           30           40           50
    CGACCATGAG   AGATAAGGAC   TGAGGGCCAG   GAAGGGGAAG   CGAGCCCGCC 60           70           80           90          100
    GAGAGGTGGC   GGGGACTGCT   CACGCCAAGG   GCCACAGCGG   CCGCGCTCCG 110          120          130          140          150
    GCCTCGCTCC   GCCGCTCCAC   GCCTCGCGGG   ATCCGCGGGG   GCAGCCCGGC
```

|     | 159 |     |     | 168 |     |     | 177 |     |     | 186 |     |     | 195 |
| --- | --- | --- | --- | --- | --- | --- | --- | --- | --- | --- | --- | --- | --- |
| CGGGCGGGG | ATG | CCG | GGG | CTG | GGG | CGG | AGG | GCG | CAG | TGG | CTG | TGC |
|     | MET | Pro | Gly | Leu | Gly | Arg | Arg | Ala | Gln | Trp | Leu | Cys |
|     | (1) |

|     | 204 |     |     | 213 |     |     | 222 |     |     | 231 |     |     | 240 |
| --- | --- | --- | --- | --- | --- | --- | --- | --- | --- | --- | --- | --- | --- |
| TGG | TGG | TGG | GGG | CTG | CTG | TGC | AGC | TGC | TGC | GGG | CCC | CCG | CCG | CTG |
| Trp | Trp | Trp | Gly | Leu | Leu | Cys | Ser | Cys | Cys | Gly | Pro | Pro | Pro | Leu |

|     | 249 |     |     | 258 |     |     | 267 |     |     | 276 |     |     | 285 |
| --- | --- | --- | --- | --- | --- | --- | --- | --- | --- | --- | --- | --- | --- |
| CGG | CCG | CCC | TTG | CCC | GCT | GCC | GCG | GCC | GCC | GCC | GCC | GGG | GGG | CAG |
| Arg | Pro | Pro | Leu | Pro | Ala | Ala | Ala | Ala | Ala | Ala | Ala | Gly | Gly | Gln |

|     | 294 |     |     | 303 |     |     | 312 |     |     | 321 |     |     | 330 |
| --- | --- | --- | --- | --- | --- | --- | --- | --- | --- | --- | --- | --- | --- |
| CTG | CTG | GGG | GAC | GGC | GGG | AGC | CCC | GGC | CGC | ACG | GAG | CAG | CCG | CCG |
| Leu | Leu | Gly | Asp | Gly | Gly | Ser | Pro | Gly | Arg | Thr | Glu | Gln | Pro | Pro |

|     | 339 |     |     | 348 |     |     | 357 |     |     | 366 |     |     | 375 |
| --- | --- | --- | --- | --- | --- | --- | --- | --- | --- | --- | --- | --- | --- |
| CCG | TCG | CCG | CAG | TCC | TCC | TCG | GGC | TTC | CTG | TAC | CGG | CGG | CTC | AAG |
| Pro | Ser | Pro | Gln | Ser | Ser | Ser | Gly | Phe | Leu | Tyr | Arg | Arg | Leu | Lys |

|     | 384 |     |     | 393 |     |     | 402 |     |     | 411 |     |     | 420 |
| --- | --- | --- | --- | --- | --- | --- | --- | --- | --- | --- | --- | --- | --- |
| ACG | CAG | GAG | AAG | CGG | GAG | ATG | CAG | AAG | GAG | ATC | TTG | TCG | GTG | CTG |
| Thr | Gln | Glu | Lys | Arg | Glu | MET | Gln | Lys | Glu | Ile | Leu | Ser | Val | Leu |

|     | 429 |     |     | 438 |     |     | 447 |     |     | 456 |     |     | 465 |
| --- | --- | --- | --- | --- | --- | --- | --- | --- | --- | --- | --- | --- | --- |
| GGG | CTC | CCG | CAC | CGG | CCC | CGG | CCC | CTG | CAC | GGC | CTC | CAA | CAG | CCG |
| Gly | Leu | Pro | His | Arg | Pro | Arg | Pro | Leu | His | Gly | Leu | Gln | Gln | Pro |

|     | 474 |     |     | 483 |     |     | 492 |     |     | 501 |     |     | 510 |
| --- | --- | --- | --- | --- | --- | --- | --- | --- | --- | --- | --- | --- | --- |
| CAG | CCC | CCG | GCG | CTC | CGG | CAG | CAG | GAG | GAG | CAG | CAG | CAG | CAG | CAG |
| Gln | Pro | Pro | Ala | Leu | Arg | Gln | Gln | Glu | Glu | Gln | Gln | Gln | Gln | Gln |

|     | 519 |     |     | 528 |     |     | 537 |     |     | 546 |     |     | 555 |
| --- | --- | --- | --- | --- | --- | --- | --- | --- | --- | --- | --- | --- | --- |
| CAG | CTG | CCT | CGC | GGA | GAG | CCC | CCT | CCC | GGG | CGA | CTG | AAG | TCC | GCG |
| Gln | Leu | Pro | Arg | Gly | Glu | Pro | Pro | Pro | Gly | Arg | Leu | Lys | Ser | Ala |

|     | 564 |     |     | 573 |     |     | 582 |     |     | 591 |     |     | 600 |
| --- | --- | --- | --- | --- | --- | --- | --- | --- | --- | --- | --- | --- | --- |
| CCC | CTC | TTC | ATG | CTG | GAT | CTG | TAC | AAC | GCC | CTG | TCC | GCC | GAC | AAC |
| Pro | Leu | Phe | MET | Leu | Asp | Leu | Tyr | Asn | Ala | Leu | Ser | Ala | Asp | Asn |

|     | 609 |     |     | 618 |     |     | 627 |     |     | 636 |     |     | 645 |
| --- | --- | --- | --- | --- | --- | --- | --- | --- | --- | --- | --- | --- | --- |
| GAC | GAG | GAC | GGG | GCG | TCG | GAG | GGG | GAG | AGG | CAG | CAG | TCC | TGG | CCC |
| Asp | Glu | Asp | Gly | Ala | Ser | Glu | Gly | Glu | Arg | Gln | Gln | Ser | Trp | Pro |

FIGURE 3A

```
     654         663         672         681         690
CAC GAA GCA GCC AGC TCG TCC CAG CGT CGG CAG CCG CCC CCG GGC
His Glu Ala Ala Ser Ser Ser Gln Arg Arg Gln Pro Pro Pro Gly Ser 699         708         717         726         735
GCC GCG CAC CCG CTC AAC CGC AAG AGC CTT CTG GCC CCC GGA TCT
Pro Pro Gly Ala Ala His Pro Leu Asn Arg Lys Ser Leu Leu Ala 744         753         762         771         780
GGC AGC GGC GGC GCG TCC CCA CTG ACC AGC GCG CAG GAC AGC GCC
Gly Ser Gly Gly Ala Ser Pro Leu Thr Ser Ala Gln Asp Ser Ala 789         798         807         816         825
TTC CTC AAC GAC GCG GAC ATG GTC ATG AGC TTT GTG AAC CTG GTG
Phe Leu Asn Asp Ala Asp MET Val MET Ser Phe Val Asn Leu Val 834         843         852         861         870
GAG TAC GAC AAG GAG TTC TCC CCT CGT CAG CGA CAC CAC AAA GAG
Glu Tyr Asp Lys Glu Phe Ser Pro Arg Gln Arg His His Lys Glu 879         888         897         906         915
TTC AAG TTC AAC TTA TCC CAG ATT CCT GAG GGT GAG GTG GTG ACG
Phe Lys Phe Asn Leu Ser Gln Ile Pro Glu Gly Glu Val Val Thr 924         933         942         951         960
GCT GCA GAA TTC CGC ATC TAC AAG GAC TGT GTT ATG GGG AGT TTT
Phe Arg Ile Tyr Lys Asp Cys Val MET Ala Ala Glu Gly Ser Phe 969         978         987         996        1005
AAA AAC CAA ACT TTT CTT ATC AGC ATT TAT CAA GTC TTA CAG GAG
Lys Asn Gln Thr Phe Leu Ile Ser Ile Tyr Gln Val Leu Gln Glu 1014        1023        1032        1041        1050
CAT CAG CAC AGA GAC TCT GAC CTG TTT TTG TTG GAC ACC CGT GTA
His Gln His Arg Asp Ser Asp Leu Phe Leu Leu Asp Thr Arg Val 1059        1068        1077        1086        1095
GTA TGG GCC TCA GAA GAA GGC TGG CTG GAA TTT GAC ATC ACG GCC
Val Trp Ala Ser Glu Glu Gly Trp Leu Glu Phe Asp Ile Thr Ala 1104        1113        1122        1131        1140
ACT AGC AAT CTG TGG GTT GTG ACT CCA CAG CAT AAC ATG GGG CTT
Thr Ser Asn Leu Trp Val Val Thr Pro Gln His Asn MET Gly Leu 1149        1158        1167        1176        1185
CAG CTG AGC GTG GTG ACA AGG GAT GGA GTC CAC GTC CAC CCC CGA
Gln Leu Ser Val Val Thr Arg Asp Gly Val His Val His Pro Arg 1194        1203        1212        1221        1230
GCC GCA GGC CTG GTG GGC AGA GAC GGC CCT TAC GAT AAG CAG CCC
Ala Ala Gly Leu Val Gly Arg Asp Gly Pro Tyr Asp Lys Gln Pro 1239        1248        1257        1266        1275
TTC ATG GTG GCT TTC TTC AAA GTG AGT GAG GTC CAC GTG CGC ACC
Phe MET Val Ala Phe Phe Lys Val Ser Glu Val His Val Arg Thr
```

FIGURE 3B

```
          1284          1293          1302          1311          1320
ACC AGG TCA GCC TCC AGC CGG CGC CGA CAA CAG AGT CGT AAT CGC
Thr Arg Ser Ala Ser Ser Arg Arg Arg Gln Gln Ser Arg Asn Arg
                                               (382)
          1329          1338          1347          1356          1365
TCT ACC CAG TCC CAG GAC GTG GCG CGG GTC TCC AGT GCT TCA GAT
Ser Thr Gln Ser Gln Asp Val Ala Arg Val Ser Ser Ala Ser Asp
(388)

1374          1383          1392          1401          1410
TAC AAC AGC AGT GAA TTG AAA ACA GCC TGC AGG AAG CAT GAG CTG
Tyr Asn Ser Ser Glu Leu Lys Thr Ala Cys Arg Lys His Glu Leu
                                   (412)
          1419          1428          1437          1446          1455
TAT GTG AGT TTC CAA GAC CTG GGA TGG CAG GAC TGG ATC ATT GCA
Tyr Val Ser Phe Gln Asp Leu Gly Trp Gln Asp Trp Ile Ile Ala 1464          1473          1482          1491          1500
CCC AAG GGC TAT GCT GCC AAT TAC TGT GAT GGA GAA TGC TCC TTC
Pro Lys Gly Tyr Ala Ala Asn Tyr Cys Asp Gly Glu Cys Ser Phe 1509          1518          1527          1536          1545
CCA CTC AAC GCA CAC ATG AAT GCA ACC AAC CAC GCG ATT GTG CAG
Pro Leu Asn Ala His MET Asn Ala Thr Asn His Ala Ile Val Gln 1554          1563          1572          1581          1590
ACC TTG GTT CAC CTT ATG AAC CCC GAG TAT GTC CCC AAA CCG TGC
Thr Leu Val His Leu MET Asn Pro Glu Tyr Val Pro Lys Pro Cys 1599          1608          1617          1626          1635
TGT GCG CCA ACT AAG CTA AAT GCC ATC TCG GTT CTT TAC TTT GAT
Cys Ala Pro Thr Lys Leu Asn Ala Ile Ser Val Leu Tyr Phe Asp 1644          1653          1662          1671          1680
GAC AAC TCC AAT GTC ATT CTG AAA AAA TAC AGG AAT ATG GTT GTA
Asp Asn Ser Asn Val Ile Leu Lys Lys Tyr Arg Asn MET Val Val 1689          1698          1708          1718          1728
AGA GCT TGT GGA TGC CAC TAACTCGAAA CCAGATGCTG GGACACACA
Arg Ala Cys Gly Cys His
                         (513)

1738          1748          1758          1768          1778
     TTCTGCCTTG GATTCCTAGA TTACATCTGC CTTAAAAAAA CACGGAAGCA 1788          1798          1808          1818          1828
     CAGTTGGAGG TGGGACGATG AGACTTTGAA ACTATCTCAT GCCAGTGCCT 1838          1848          1858          1868          1878
     TATTACCCAG GAAGATTTTA AAGGACCTCA TTAATAATTT GCTCACTTGG 1888          1898          1908          1918          1928
     TAAATGACGT GAGTAGTTGT TGGTCTGTAG CAAGCTGAGT TTGGATGTCT
```

FIGURE 3C

```
          1938       1948       1958       1968       1978
     GTAGCATAAG GTCTGGTAAC TGCAGAAACA TAACCGTGAA GCTCTTCCTA 1988       1998       2008       2018       2028
     CCCTCCTCCC CCAAAAACCC ACCAAAATTA GTTTTAGCTG TAGATCAAGC 2038       2048       2058       2068       2078
     TATTTGGGGT GTTTGTTAGT AAATAGGGAA AATAATCTCA AAGGAGTTAA 2088       2098       2108       2118       2128
     ATGTATTCTT GGCTAAAGGA TCAGCTGGTT CAGTACTGTC TATCAAAGGT 2138       2148       2158       2168       2178
     AGATTTTACA GAGAACAGAA ATCGGGGAAG TGGGGGGAAC GCCTCTGTTC 2188       2198       2208       2218       2228
     AGTTCATTCC CAGAAGTCCA CAGGACGCAC AGCCCAGGCC ACAGCCAGGG 2238       2248       2258       2268       2278
     CTCCACGGGG CGCCCTTGTC TCAGTCATTG CTGTTGTATG TTCGTGCTGG 2288       2298       2308       2318       2328
     AGTTTTGTTG GTGTGAAAAT ACACTTATTT CAGCCAAAAC ATACCATTTC 2338       2348       2358       2368       2378
     TACACCTCAA TCCTCCATTT GCTGTACTCT TTGCTAGTAC CAAAAGTAGA 2388       2398       2408       2418       2428
     CTGATTACAC TGAGGTGAGG CTACAAGGGG TGTGTAACCG TGTAACACGT 2438       2448       2458       2468       2478
     GAAGGCAGTG CTCACCTCTT CTTTACCAGA ACGGTTCTTT GACCAGCACA 2488       2498       2508       2518       2528
     TTAACTTCTG GACTGCCGGC TCTAGTACCT TTTCAGTAAA GTGGTTCTCT 2538       2548       2558       2568       2578
     GCCTTTTTAC TATACAGCAT ACCACGCCAC AGGGTTAGAA CCAACGAAGA 2588       2598       2608       2618       2628
     AAATAAAATG AGGGTGCCCA GCTTATAAGA ATGGTGTTAG GGGGATGAGC 2638       2648       2658       2668       2678
     ATGCTGTTTA TGAACGGAAA TCATGATTTC CCTGTAGAAA GTGAGGCTCA 2688       2698       2708       2718       2728
     GATTAAATTT TAGAATATTT TCTAAATGTC TTTTTCACAA TCATGTGACT 2738       2748       2758       2768       2778
     GGGAAGGCAA TTTCATACTA AACTGATTAA ATAATACATT TATAATCTAC 2788       2798       2808       2818       2828
     AACTGTTTGC ACTTACAGCT TTTTTTGTAA ATATAAACTA TAATTTATTG
```

FIGURE 3D

```
      2838       2848       2858       2868       2878
TCTATTTTAT ATCTGTTTTG CTGTGGCGTT GGGGGGGGGG CCGGGCTTTT 2888       2898       2908       2918
GGGGGGGGGG GTTTGTTTGG GGGGTGTCGT GGTGTGGGCG GGCGG
```

5,459,047

BMP-6 PROTEINS

CROSS-REFERENCE TO RELATED APPLICATIONS

This application is a divisional of U.S. Ser. No. 926,081 filed Aug. 5, 1992, which is a divisional of U.S. Ser. No. 490,033 filed Mar. 7, 199, now U.S. Pat. No. 5,187,076, which is a continuation-in-part of U.S. Ser. No. 370,544 filed Jun. 23, 1989, which is a continuation-in-part of U.S. Ser. No. 347,559 filed May 4, 1989 (now abandoned), which is a continuation-in-part of U.S. Ser. Nos. 179,100; 179,101 (now abandoned); and 179,197 all filed Apr. 8, 1988, which are continuations-in-part of U.S. Ser. Nos. 028,285 filed Mar. 20, 1987 (now abandoned); and 031,346 filed Mar. 26, 1987, now U.S. Pat. No. 4,877,864, which are continuations-in-part of U.S. Ser. Nos. 943,332 filed Dec. 17, 1986 (now abandoned;) and 880,776 filed Jul. 1, 1986 (now abandoned).

The present invention relates to a family of purified proteins, termed BMP-6 proteins (wherein BMP is bone morphogenic protein), which exhibit the ability to induce cartilage and/or bone formation and processes for obtaining them. These proteins may be used to induce bone and/or cartilage formation and in wound healing and tissue repair.

The invention provides purified human BMP-6 proteins, substantially free from other proteins with which they are co-produced. The BMP-6 proteins of the invention are characterized by an amino acid sequence comprising acid #412 to amino acid #513 set forth in Table III. The amino acid sequence from amino acid #412 to #513 is encoded by the DNA sequence of Table III from nucleotide #1393 to nucleotide #1698. These proteins may be further characterized by an apparent molecular weight of 28,000–30,000 daltons as determined by sodium dodecyl sulfate polyacrylamide gel electrophoresis (SDS-PAGE). Under reducing conditions in SDS-PAGE the protein electrophoreses with a molecular weight of approximately 14,000–20,000 daltons. It is contemplated that these proteins are capable of stimulating promoting, or otherwise inducing cartilage and/or bone formation.

The invention further provides bovine BMP-6 proteins characterized by the amino acid sequence comprising amino acid #121 to amino acid #222 set forth in Table II. The amino acid sequence from #121 to #222 is encoded by the DNA sequence of Table II from nucleotide #361 to #666 of Table II. These proteins may be further characterized by an apparent molecular weight of 28,000–30,000 daltons as determined by sodium dodecyl sulfate polyacrylamide gel electrophoresis (SDS-PAGE). Under reducing conditions in SDS-PAGE the protein electrophoreses with a molecular weight of approximately 14,000–20,000 daltons. It is contemplated that these proteins are capable of inducing cartilage and/or bone formation.

Human BMP-6 proteins of the invention are produced by culturing a cell transformed with a DNA sequence comprising nucleotide #1393 to nucleotide #1698 as shown in Table III or a substantially similar sequence, recovering and purifying from the culture medium a protein comprising amino acid #412 to amino acid #513 or a substantially similar sequence.

Bovine proteins of the invention may be produced by culturing a cell transformed with a DNA comprising nucleotide #361 through nucleotide #666 as set forth in Table II or a substantially similar sequence and recovering and purifying from the culture medium a protein comprising amino acid #121 to amino acid #222 as set forth in Table II.

The invention further provides a method wherein the proteins described above are utilized for obtaining related human protein/s or other mammalian cartilage and/or bone formation protein/s. Such methods are known to those skilled in the art of genetic engineering. One method for obtaining such proteins involves utilizing the human BMP-6 coding sequence or a portion thereof from nucleotide #160–#1698 to design probes for screening human genomic and/or cDNA libraries to isolate human genomic and/or cDNA sequences. Additional methods within the art may employ the bovine and human BMP-6 proteins of the invention to obtain other mammalian BMP-6 cartilage and/or bone formation proteins. Having identified the nucleotide sequences, the proteins are produced by culturing a cell transformed with the nucleotide sequence. This sequence or portions thereof hybridizes under stringent conditions to the nucleotide sequence substantially as shown in Table II comprising nucleotide #1 to nucleotide #666 or the nucleotide sequence or portions thereof substantially as shown in Table III comprising nucleotide #160 to #1698 and encodes a protein exhibiting cartilage and/or bone formation activity. The expressed protein is recovered and purified from the culture medium. The purified BMP-6 proteins of the invention are substantially free from other proteinaceous materials with which they are co-produced, as well as from other contaminants.

The BMP-6 proteins of the invention are further characterized by the ability to promote, stimulate or otherwise induce the formation of cartilage and/or bone. It is further contemplated that the ability of these proteins to induce the formation of cartilage and/or bone is exhibited by the ability to demonstrate cartilage and/or bone formation activity in the rat bone formation assay described below. It is further contemplated that the proteins of the invention demonstrate activity in this rat bone formation assay at a concentration of 10 µg–500 µg/gram of bone formed. More particularly, it is contemplated these proteins may be characterized by the ability of 1 µg of the protein to score at least +2 in the rat bone formation assay described below using either the original or modified scoring method.

Another aspect Of the invention provides pharmaceutical compositions containing a therapeutically effective amount of a protein of the invention in a pharmaceutically acceptable vehicle or carrier. These compositions of the invention may be used to induce bone and/or cartilage formation. These compositions may also be used for wound healing and tissue repair. Further compositions of the invention may include, in addition to a BMP-6 protein, at least one other therapeutically useful agent such as the proteins designated BMP-1, BMP-2A and -2B, BMP-3, BMP-5, and BMP-7 disclosed respectively in co-owned U.S. patent applications Ser. Nos. 179,101, 179,100, and 179,197, 437,409, 438,919. Other therapeutically useful agents include growth factors such as epidermal growth factor (EGF), fibroblast growth factor (FGF), transforming growth factors (TGF-α and TGF-β) and platelet derived growth factor (PDGF). The compositions of the invention may also include an appropriate matrix, for instance, for delivery and support of the composition and/or providing a surface for bone and/or cartilage growth.

The compositions may be employed in methods for treating a number of bone and/or cartilage defects, and periodontal disease. They may also be employed in methods for treating various types of wounds and in tissue repair. These methods, according to the invention, entail administering to a patient needing such bone and/or cartilage formation, wound healing or tissue repair, a therapeutically effective amount of a BMP-6 protein of the invention in a pharmaceutically acceptable vehicle or carrier including a martrix. These methods may also entail the administration of a BMP-6 protein in conjunction with at least one of the "BMP" proteins disclosed in the co-owned applications described above. In addition, these methods may also include the administration of a protein of the invention with other growth factors including EGF, FGF, TGF-α, TGF-β, and PDFG.

Still a further aspect of the invention are DNA sequences coding for expression of a protein of the invention. Such sequences include the sequence of nucleotides in a 5' to 3' direction illustrated in Table II or Table III or DNA sequences which hybridize under stringent conditions with the DNA sequence of Table II or Table III and encode a protein demonstrating ability to induce cartilage and/or bone formation. Such ability to induce cartilage and/or bone formation may be demonstrated in the rat bone formation assay described below. It is contemplated that these proteins demonstrate activity in this assay at a concentration of 10 μg–500 μg/gram of bone formed. More particularly, it is contemplated that these proteins demonstrate the ability of 1 μg of the protein to score at least +2 in the rat bone formation assay using either the original or modified scoring method. Allelic or variations as described herein below of the sequences of Table II and III, whether such nucleotide changes result in changes in the peptide sequence or not, are also included in the present invention.

A further aspect of the invention provides vectors containing a DNA sequence as described above in operative association with an expression control sequence therefor. These vectors may be employed in a novel process for producing a protein of the invention in which a cell line transformed with a DNA sequence directing expression of a protein of the invention in operative association with an expression control sequence therefor, is cultured in a suitable culture medium and a protein of the invention is isolated and purified therefrom. This claimed process may employ a number of known cells, both prokaryotic and eukaryotic, as host cells for expression of the polypeptide.

Other aspects and advantages of the present invention will be apparent upon consideration of the following detailed description and preferred embodiments thereof.

BRIEF DESCRIPTION OF THE DRAWING

FIG. 1 comprises DNA sequence and derived amino acid sequence of bovine BMP-5.

FIG. 1 corresponds to Table I further described below.

FIG. 2 comprises DNA sequence and derived amino acid sequence of bovine BMP-6.

FIG. 2 corresponds to Table II further described below.

FIG. 3 comprises DNA sequence and derived amino acid sequence of human BMP-6 from BMP6C35 ATCC #68245. FIG. 3 corresponds to Table III further described below.

DETAILED DESCRIPTION OF THE INVENTION

The purified human BMP-6 proteins of the invention are characterized by an amino acid sequence comprising amino acid #412 to #513 as set forth in Table III. In one embodiment a BMP-6 protein of the invention comprises amino acid #388 to #513 of Table III. In a further embodiment the BMP-6 protein comprises amino acid #382 to #513 of Table III.

The purified BMP-6 human cartilage/bone proteins of the present invention may be produced by culturing a host cell transformed with a DNA sequence comprising nucleotide #1393 to nucleotide #1698 as set forth in Table III or substantially homologous sequences operatively linked to a heterologous regulatory control sequence and recovering, isolating and purifying from the culture medium a protein comprising amino acid #412 to amino acid #513 as set forth in Table III or a substantially homologous sequence.

In another embodiment, purified human BMP-6 proteins may be produced by culturing a host cell transformed with a DNA sequence comprising nucleotide #1321 to #1698 as set forth in Table III or substantially homologous sequences operatively linked to a heterologous regulatory control sequence and recovering and purifying from the culture medium a protein comprising amino acid #388 to #513 asset forth in Table III or a substantially homologous sequence.

In another embodiment, purified human BMP-6 proteins may be produced by culturing a host cell transformed with a DNA sequence comprising nucleotide #1303 to #1698 as set forth in Table III or substantially homologous sequences operatively linked to a heterologous regulatory control sequence and recovering and purifying from the culture medium a protein comprising amino acid #382 to #513 as set forth in Table III or a substantially homologous sequence.

The purified human BMP-6 proteins are substantially free from other proteinaceous materials with which they are co-produced, as well as-from other contaminants.

Purified BMP-6 bovine cartilage/bone protein of the present invention are produced by culturing a host cell transformed with a DNA sequence comprising nucleotide #361 to nucleotide #666 as set forth in Table II or substantially homologous sequences and recovering from the culture medium a protein comprising amino acid #121 to amino acid #222 as set forth in Table II or a substantially homologous sequence. In another embodiment the bovine protein is produced by culturing a host cell transformed with a sequence comprising nucleotide #289 to #666 of Table II and recovering and purifying a protein comprising amino acid #97 to amino acid #222. The purified BMP-6 bovine proteins are substantially free from other proteinaceous materials with which they are co-produced, as well as from other contaminants.

These proteins of the invention may be further characterized by the ability to demonstrate cartilage and/or bone formation activity. This activity may be demonstrated, for example, in the rat bone formation assay as described in Example III. It is further contemplated that these proteins demonstrate activity in the assay at a concentration of 10 μg–500 μg/gram of bone formed. The proteins may be further characterized by the ability of 1 μg to score at least +2 in this assay.

BMP-6 proteins may be further characterized by an apparent molecular weight of 28,000–30,000 daltons as determined by sodium dodecyl sulfate polyacrylamide gel electrophoresis (SDS-PAGE). Under reducing conditions in SDS-PAGE, the protein electrophoreses with a, molecular weight of approximately 14,000–20,000 daltons.

The proteins provided herein also include factors encoded by the sequences similar to those of Table II and Table III but into Which modifications are naturally provided (e.g. allelic variations in the nucleotide sequence which may result in amino acid changes in the polypeptide) or deliberately engineered. Similarly, synthetic polypeptides which wholly or partially duplicate continuous sequences of the amino acid residues of Table II or Table III are encompassed by the invention. These sequences, by virtue of sharing primary, secondary, or tertiary structural and conformational characteristics with other cartilage/bone proteins of the invention may possess bone and/or cartilage growth factor biological properties in common therewith. Thus, they may be employed as biologically active substitutes for naturally-occurring proteins in therapeutic processes.

Other specific mutations of the sequences of the proteins of the invention described herein may involve modifications of a glycosylation site. These modifications may involve O-linked or N-linked glycosylation sites. For instance, the absence of glycosylation or only partial glycosylation at the asparagine-linked glycosylation sites results from amino acid substitution or deletion at the asparagine-linked glycosylation recognition sites present in the sequences of the proteins of the invention, for example, as shown in Table II or Table III. The asparagine-linked glycosylation recognition sites comprise tripeptide sequences which are specifically recognized by appropriate cellular glycosylation enzymes. These tripeptide sequences are either asparagine-X-threonine or asparagine-X-serine, where X is usually any amino acid. A variety of amino acid substitutions or deletions at one or both of the first or third amino acid positions of a glycosylation recognition site (and/or amino acid deletion at the second position) results in non-glycosylation at the modified tripeptide sequence. Expression of such altered nucleotide sequences produces variants which are not glycosylated at that site.

The present invention also encompasses the novel DNA sequences, free of association with DNA sequences encoding other proteinaceous materials, and coding on expression for the proteins of the invention. These DNA sequences include those depicted in Tables II and III in a 5' to 3' direction or portions thereof. Further included are those sequences which hybridize under, stringent hybridization conditions [see, T. Maniatis et al, *Molecular Cloning (A Laboratory Manual)*, Cold Spring. Harbor Laboratory (1982), pages 387 to 389] to the DNA sequence of Table II or Table III and demonstrate cartilage and/or bone formation activity. Such cartilage and/Or bone formation activity may be in the rat bone formation assay. An example of one such stringent hybridization condition is hybridization at 4× SSC at 65° C., followed by a washing in 0.1× SCC at 65° C. for an hour. Alternatively, an exemplary stringent hybridization condition is in 50% formamide, 4× SCC at 42° C.

Similarly, DNA sequences which encode proteins similar to the protein encoded by the sequence of Table II or Table III, but which differ in codon sequence due to the degeneracies of the genetic code or allelic variations (naturally-occurring base changes in the species population which may or may not result in an amino acid change) also encode the proteins of the invention described herein. Variations in the DNA sequences of Table II and Table III which are caused by point mutations or by induced modifications (including insertion, deletion, and substitution) to enhance the activity, half-life or production of the polypeptides encoded thereby are also encompassed in the invention.

In a further aspect, the invention provides a method for obtaining related human proteins or other mammalian BMP-6 proteins. One method for obtaining such proteins entails, for instance, utilizing the human BMP-6 coding sequence disclosed herein to probe a human genomic library using standard techniques for the human gene or fragments thereof. Sequences thus identified may also be used as probes to identify a human cell line or tissue which synthesizes the analogous cartilage/bone protein. A cDNA library is synthesized and screened with probes derived from the human or bovine coding sequences. The human sequence thus identified is transformed into a host cell, the host cell is cultured and the protein recovered, isolated and purified from the culture medium. The purified protein is predicted to exhibit cartilage and/or bone formation activity. This activity may be demonstrated in the rat bone formation assay of Example III.

Another aspect of the present invention provides a novel method for producing the proteins of the invention. This method involves culturing a suitable cell line, which has been transformed with a DNA sequence coding for expression of a protein of the invention, under the control of known regulatory sequences. Regulatory sequences include promoter fragments, terminator fragments and other suitable sequences which direct the expression of the protein in an appropriate host cell. Methods for culturing suitable cell lines are within the skill of the art. The transformed cells are cultured and the BMP-6 proteins expressed thereby are recovered and purified from the culture medium using purification techniques known to those skilled in the art. The purified BMP-6 proteins are substantially free from other proteinaceous materials with which they are co-produced, as well as other contaminants. Purified BMP-6 proteins of the invention are substantially free from materials with which the proteins of the invention exist in nature.

Suitable cells or cell lines may be mammalian cells, such as Chinese hamster ovary cells (CHO). The selection of suitable mammalian host cells and methods for transformation, culture, amplification, screening and product production and purification are known in the art. See, e.g., Gething and Sambrook, *Nature*, 293:620–625 (1981), or alternatively, Kaufman et al, *Mol. Cell. Biol.*, 5(7):1750–1759 (1985) or Howley et al, U.S. Pat. No. 4,419,446. Other suitable mammalian cell lines are the monkey COS-1 cell line and the CV-1 cell line.

Bacterial cells may also be suitable hosts. For example, the various strains of *E. coli* (e.g., HB101, MC1061) are well-known as host ,cells in the field of biotechnology. Various strains of *B. subtilis*, Pseudomonas, other bacilli and the like may also be employed in this method.

Many strains of yeast cells known to those skilled in the art may also be available as host cells for expression of the polypeptides of the present invention. Additionally, where desired, insect cells may be utilized as host cells in the method of the present invention. See, e.g. Miller et al, *Genetic Engineering*, 8:277–298 (Plenum Press 1986) and references cited therein.

Another aspect of the present invention provides vectors for use in the method of expression of the proteins of the invention. Preferably the vectors contain the full novel DNA sequences described above which code for the novel BMP-6 proteins of the invention. Additionally the vectors also contain appropriate expression control sequences permitting expression of the protein sequences. Alternatively, vectors incorporating modified sequences as described above are also embodiments of the present invention and useful in the production of the proteins of the invention. The vectors may be employed in the method of transforming cell lines and contain selected regulatory sequences in operative association with the DNA coding sequences of the invention which are capable of directing the replication and expression thereof in selected host cells. Useful regulatory sequences for such vectors are known to those skilled in the art may be selected depending upon the selected host cells. Such selection is routine and does not form part of the present invention. Host cells transformed with such vectors and progeny thereof for use in producing BMP-6 proteins are also provided by the invention.

A protein of the present invention, which induces cartilage and/or bone formation in circumstances where bone and/or cartilage is not normally formed, has application in the healing of bone fractures and cartilage defects in humans and other animals. Such a preparation employing a protein of the invention may have prophylactic use in closed as well as open fracture reduction and also in the improved fixation of artificial joints. De novo bone formation induced by an osteogenic agent contributes to the repair of congenital, trauma induced, or oncologic resection induced craniofacial defects, and also is useful in cosmetic plastic surgery. A protein of the invention may be used in the treatment of periodontal disease, and in other tooth repair processes. Such agents may provide an environment to attract bone-forming cells, stimulate growth of bone-forming cells or induce differentiation of progenitors of bone-forming cells. A variety of osteogenic, cartilage-inducing and bone inducing factors have been described. See, e.g. European patent applications 148,155 and 169,016 for discussions thereof.

The proteins of the invention may also be used in wound healing and related tissue repair. The types of wounds include, but are not limited to burns, incisions and ulcers. (See, e.g. PCT Publication W084/01106 for discussion of wound healing and related tissue repair).

A further aspect of the invention is a therapeutic method and composition for repairing fractures and other conditions related to bone and/or cartilage defects or periodontal diseases. In addition, the invention comprises therapeutic methods and compositions for wound healing and tissue repair. Such compositions comprise a therapeutically effective amount of at least one of the BMP-6 proteins of the invention in admixture with a pharmaceutically acceptable vehicle, carrier or matrix.

It is expected that the proteins of the invention may act in concert with or perhaps synergistically with one another or with other related proteins and growth factors. Therapeutic methods and compositions of the invention therefore comprise one or more of the proteins of the present invention. Further therapeutic methods and compositions of the invention therefore, comprise a therapeutic amount of at least one protein of the invention with a therapeutic amount of at least one of the other "BMP" proteins, BMP-1, BMP-2 (BMP-2A, BMP-2 Class I), BMP-3, BMP-4 (BMP-2B, BMP-2 Class II), BMP-5 and BMP-7, disclosed in co-owned and co-pending U.S. applications described above. Such methods and compositions of the invention may comprise proteins of the invention or portions thereof in combination with the abovementioned "BMP" proteins or portions thereof. Such combination may comprise individual separate molecules from each of the proteins or heteromolecules such as heterodimers formed by portions of the respective proteins. For example, a method and composition of the invention may comprise a BMP-6 protein of the invention or a portion thereof linked with a portion of a different "BMP" protein to form a heteromolecule.

Further therapeutic methods and compositions of the invention comprise the proteins of the invention or portions thereof in combination with other agents beneficial to the treatment of the bone and/or cartilage defect, wound, or tissue in question. These agents include various growth factors such as epidermal growth factor (EGF), fibroblast growth factor (FGF), platelet derived growth factor (PDGF), transforming growth factors (TGF-α and TGF-β), k-fibroblast growth factor (kFGF), parathyroid hormone (PTH), leukemia inhibitory factor (LIF/HILDA/DIA), and insulin-like growth factors (IGF-I and IGF-II). Portions of these agents may also be used in compositions of the invention.

The preparation and formulation of such physiologically acceptable protein compositions, having due regard to pH, isotonicity, stability and the like, is within the skill of the art. The therapeutic compositions are also presently valuable for veterinary applications due to the apparent lack of species specificity in cartilage and bone proteins. Domestic animals and thoroughbred horses in addition to humans are desired patients for such treatment with the proteins of the present invention.

The therapeutic method includes administering the composition topically, systematically, or locally as an implant or device. When administered, the therapeutic composition for use in this invention is, of course, in a pyrogen-free, physiologically acceptable form. Further, the composition may desirably be encapsulated or injected in a viscous form for delivery to the site of cartilage and/or bone or tissue damage. Topical administration may be suitable for wound healing and tissue repair. Preferably for bone and/or cartilage formation, the composition includes a matrix capable of delivering the cartilage/bone proteins of the invention to the site of bone and/or cartilage damage, providing a structure for the developing bone and cartilage and optimally capable of being resorbed into the body. Matrices may provide slow release of the cartilage and/or bone inductive proteins proper presentation and appropriate environment for cellular infiltration. Matrices may be formed of materials presently in use for other implanted medical applications.

The choice of matrix material is based on biocompatibility, biodegradability, mechanical properties, cosmetic appearance and interface properties. The particular application of the compositions of the invention will define the appropriate formulation. Potential matrices for the compositions are biodegradable and chemically defined calcium sulfate, tricalciumphosphate, hydroxyapatite, polylactic acid and polyanhydrides. Other potential materials are biodegradable and biologically well defined, such as bone or dermal collagen. Further matrices are comprised of pure proteins or extracellular matrix components. Other potential matrices are nonbiodegradable and chemically defined, such as sintered hydroxyapatite, bioglass, aluminates, or other ceramics. Matrices may, be comprised of combinations of any of the above mentioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability.

The dosage regimen will be determined by the attending physician considering various factors which modify the action of the proteins of the invention. Factors which may modify the action of the proteins of the invention include the amount of bone weight desired to be formed, the site of bone damage, the condition of the damaged bone, the size of a wound, type of damaged tissue, the patient's age, sex, and diet, the severity of any infection, time of administration and other clinical factors. The dosage may vary with the type of matrix used in the reconstitution and the type or types of bone and/or cartilage proteins present in the composition. The addition of other known growth factors, such as EGF, PDGF, TGF-α, TGF-β, and IGF-I to the final composition, may also effect the dosage.

Progress can be monitored by periodic assessment of cartilage and/or bone growth and/or repair. The progress can be monitored, for example, using x-rays, histomorphometric determinations and tetracycline labeling.

The following examples illustrate practice of the present invention in recovering and characterizing bovine cartilage and/or bone proteins of the invention and employing these proteins to recover the corresponding human protein or proteins and in expressing the proteins via recombinant techniques.

EXAMPLE I

Isolation of Bovine Cartilage/Bone Inductive Protein

Ground bovine bone powder (20–120 mesh, Helitrex) is prepared according to the procedures of M. R. Urist et al., *Proc. Natl Acad. Sci USA*, 70:3511 (1973) with elimination of some extraction steps as identified below. Ten kgs of the ground powder is demineralized in successive changes of 0.6N HCl at 4½ C over a 48 hour period with vigorous stirring. The resulting suspension is extracted for 16 hours at 4½ C with 50 liters of 2M $CaCl_2$ and 10 mM ethylenediamine-tetraacetic acid [EDTA], and followed by extraction for 4 hours in 50 liters of 0.5M EDTA. The residue is washed three times with distilled water before its resuspension in 20 liters of 4M guanidine hydrochloride [GuCl], 20 mM Tris (pH 7.4), 1 mM N-ethylmaleimide, 1 mM iodoacetamide, 1 mM phenylmethylsulfonyl fluorine as described in *Clin. Orthop. Rel. Res.*, 171: 213 (1982). After 16 to 20 hours the supernatant is removed and replaced with another 10 liters of GuCl buffer. The residue is extracted for another 24 hours.

The crude GuCl extracts are combined, concentrated approximately 20 times on a Pellicon apparatus with a 10,000 molecular weight cut-off membrane, and then dialyzed in 50 mM Tris, 0.1M NaCl, 6M urea (pH7.2), the starting buffer for the first column. After extensive dialysis the protein is loaded on a 4 liter DEAE cellulose column and the unbound fractions are collected.

The unbound fractions are concentrated and dialyzed against 50 mM NaAc, 50 mM NaCl (pH 4.6) in 6M urea. The unbound fractions are applied to a carboxymethyl cellulose column. Protein not bound to the column is removed by extensive washing with starting buffer, and the material containing protein having bone and/or cartilage formation activity as measured by the Rosen-modified Sampath Reddi assay (described in Example III below) desorbed from the column by 50 mM NaAc 0.25 mM NaCl, 6M urea (pH 4.6). The protein from this step elution is concentrated 20- to 40-fold, then diluted 5 times with 80 mM $KPO_4$, 6M urea (pH6.0). The pH of the solution is adjusted to 6.0 with 500 mM $K_2HPO_4$. The sample is applied to an hydroxylapatite column (LKB) equilibrated in 80 mM $KPO_4$, 6M urea (pH6.0) and all unbound protein is removed by washing the column with the same buffer. Protein having bone and/or cartilage formation activity is eluted with 100 mM $KPO_4$ (pH7.4) and 6M urea.

The protein is concentrated approximately 10 times, and solid NaCl added to a final concentration of 0.15M. This material is applied to a heparin—Sepharose column equilibrated in 50 mM $KPO_4$, 150 mM NaCl, 6M urea (pH7.4). After extensive washing of the column with starting buffer, a protein with bone and/or cartilage inductive activity is eluted by 50 mM $KPO_4$, 700 mM NaCl, 6M urea (pH7.4). This fraction is concentrated to a minimum volume, and 0.4 ml aliquots are applied to Superose 6 and Superose 12 columns connected in series, equilibrated with 4M GuCl, 20 mM Tris (pH7.2) and the columns developed at a flow rate of 0.25 ml/min. The protein demonstrating bone and/or cartilage inductive activity corresponds to an approximate 30,000 dalton protein.

The above fractions from the superose columns are pooled, dialyzed against 50 mM NaAc, 6M urea (pH4.6), and applied to a Pharmacia MonoS HR column. The column is developed with a gradient to 1.0M NaCl, 50 mM NaAc, 6M urea (pH4.6). Active bone and/or cartilage formation fractions are pooled. The material is applied to a 0.46×25 cm Vydac C4 column in 0.1% TFA and the column developed with a gradient to 90% acetonitrile, 0.1% TFA (31.5% acetonitrile, 0.1% TFA to 49.5% acetonitrile, 0.1% TFA in 60 minutes at 1 ml per minute). Active material is eluted at approximately 40–44% acetonitrile. Fractions were assayed for cartilage and/or bone formation activity. The active material is further fractionated on a MonoQ column. The protein is dialyzed against 6M urea, 25 mM diethanolamine, pH 8.6 and then applied to a 0.5 by 5 cm MonoQ column (Pharmacia) which is developed with a gradient of 6M urea, 25 mM diethanolamine, pH 8.6 and 0.5M NaCl, 6M urea, 25 mM diethanolamine, pH 8.6. Fractions are brought Go pH3.0 with 10% trifluoroacetic acid (TFA).

Aliquots of the appropriate fractions are iodinated by one of the following methods: P. J. McConahey et al, *Int. Arch. Allergy*, 29:185–189 (1966); A. E. Bolton et al, *Biochem J.*, 133:529 (1973); and D. F. Bowen-Pope, *J. Biol. Chem.*, 237:5161 (1982). The iodinated proteins present in these fractions are analyzed by SDS gel electrophoresis.

EXAMPLE II

Characterization of Bovine Cartilage/Bone Inductive Factor
A. Molecular Weight

Approximately 5 µg protein from Example I in 6M urea, 25 mM diethanolamine, pH 8.6, approximately 0.3M NaCl is made 0.1% with respect to SDS and dialyzed against 50 mM tris/HCl 0.1% SDS pH 7.5 for 16 hrs. The dialyzed material is then electrophoretically concentrated against a dialysis membrane [Hunkapillar et al *Meth. Enzymol.* 91: 227–236 (1983)] with a small amount of I 125 labelled counterpart. This material (volume approximately 100 µl) is loaded onto a 12% polyacrylamide gel and subjected to SDS-PAGE [Laemmli, U.K. *Nature*, 227:680–685 (1970)] without reducing the sample with dithiothreitol. The molecular weight is determined relative to prestained molecular weight standards (Bethesda Research Labs). Following autoradiography of the unfixed gel the approximate 28,000–30,000 dalton band is excised and the protein electrophoretically eluted from the gel (Hunkapillar et al supra). Based on similar purified bone fractions as described in the co-pending "BMP" applications described above wherein bone and/or cartilage activity is found in the 28,000–30,000 region, it is inferred that this band comprises bone and/or cartilage inductive fractions.

B. Subunit Characterization

The subunit composition of the isolated bovine bone protein is also determined. The eluted protein described above is fully reduced and alkylated in 2% SDS using iodoacetate and standard procedures and reconcentrated by electrophoretic packing. The fully reduced and alkylated sample is then further submitted to SDS-PAGE on a 12% gel and the resulting approximate 14,000–20,000 dalton region having a doublet appearance located by autoradiography of the unfixed gel. A faint band remains at the 28,000–30,000 region. Thus the 28,000–30,000 dalton protein yields a broad region of 14,000–20,000 which may otherwise also be interpreted and described as comprising two broad bands of approximately 14,000–16,000 and 16,000–20,000 daltons.

EXAMPLE III

Rosen Modified Sampath-Reddi Assay

A modified version of the rat bone formation assay described in Sampath and Reddi, *Proc. Natl. Acad. Sci. U.S.A.*, 80:6591–6595 (1983) is used to evaluate bone and/or cartilage activity of the proteins of the invention. This modified assay is herein called the Rosen-modified Sampath-Reddi assay. The ethanol precipitation step of the Sampath-Reddi procedure is replaced by dialyzing (if the composition is a solution) or diafiltering (if the composition is a suspension) the fraction to be assayed against water. The solution or suspension is then redissolved in 0.1 % TFA, and the resulting solution added to 20 mg of rat matrix. A mock rat matrix sample not treated with the protein serves as a control. This material is frozen and lyophilized and the resulting powder enclosed in #5 gelatin capsules. The capsules are implanted subcutaneously in the abdominal thoracic area of 21–49 day old male Long Evans rats. The implants are removed after 5–21 days. Half of each implant is used for alkaline phosphatase analysis [see, A. H. Reddi et al., *Proc. Natl Acad Sci.*, 69:1601 (1972)].

The other half of each implant is fixed and processed for histological analysis. Glycolmethacrylate sections (1 μm) are stained with Von Kossa and acid fuschin or toluidine blue to score the amount of induced bone and cartilage formation present in each implant. The terms +1 through +5 represent the area of each histological section of an implant occupied by new bone and/or cartilage cells and newly formed bone and matrix. Two scoring methods are herein described. The first describes the original scoring method while the second describes the later adopted scoring method. A score of +5 indicates that greater than 50% of the implant is new bone and/or cartilage produced as a direct result of protein in the implant. A score of +4, +3, +2 and +1 would indicate that greater than 40%, 30%, 20% and 10% respectively of the implant contains new cartilage and/or bone. The scoring method later adopted (which herein after maybe referred to as the "modified" scoring method) is as follows: Three non-adjacent sections are evaluated from each implant and averaged. "±" indicates tentative identification of cartilage or bone; "+2", >25%; "+3+", >50%; "+4", >75%; "+5", >80%. The scores of the individual implants are tabulated to indicate assay variability.

It is contemplated that the dose response nature of the cartilage and/or bone inductive protein containing samples of the matrix samples will demonstrate that the amount of bone and/or cartilage formed increases with the amount of cartilage/bone inductive protein in the sample. It is contemplated that the control samples will not result in any bone and/or cartilage formation.

As with other cartilage and/or bone inductive proteins such as the above-mentioned "BMP" proteins, the bone and/or cartilage formed is expected to be physically confined to the space occupied by the matrix. Samples are also analyzed by SDS gel electrophoresis and isoelectric focusing followed by autoradiography. The activity is correlated with the protein bands and pI. To estimate the purity of the protein in a particular fraction an extinction coefficient of 1 OD/mg-cm is used as an estimate for protein and the protein is run on SDS PAGE followed by silver staining or radioiodination and autoradiography.

EXAMPLE IV

Bovine BMP-6 Protein Composition

The gel slice of the approximate 14,000–20,000 dalton region described in Example IIB is fixed with methanol-acetic acid-water using standard procedures, briefly rinsed with water, then neutralized with 0.1M ammonium bicarbonate. Following dicing the gel slice with a razor blade, the protein is digested from the gel matrix by adding 0.2 μg of TPCK-treated trypsin (Worthington) and incubating the gel for 16 hr. at 37 degrees centigrade. The resultant digest is then subjected to RPHPLC using a C4 Vydac RPHPLC column and 0.1% TFA-water 0.1% TFA water-acetonitrile gradient. The resultant peptide peaks were monitored by UV absorbance at 214 and 280 nm and subjected to direct amino terminal amino acid sequence analysis using an Applied Biosystems gas-phase sequenator (Model 470A). One tryptic fragment is isolated by standard procedures having the following amino acid sequence as represented by the amino acid standard three-letter symbols and where "Xaa" indicates an unknown amino acid the amino acid in parentheses indicates uncertainty in the sequence:

Xaa-His-Glu-Leu-Tyr-Val-Ser-Phe-(Ser)

The following four oligonucleotide probes are designed on the basis of the amino acid sequence of the aboveidentified tryptic fragment and synthesized on an automated DNA synthesizer.

PROBE #1: GTRCTYGANATRCANTC
PROBE #2: GTRCTYGANATRCANAG
PROBE #3: GTRCTYAAYATRCANTC
PROBE #4: GTRCTYAAYATRCANAG

The standard nucleotide symbols in the above identified probes are as follows: A,adenine; C,cytosine; G,guanine; T,thymine; N, adenosine or cytosine or guanine or thymine; R,adenosine or guanine; and Y,cytosine or thymine.

Each of the probes consists of pools of oligonucleotides. Because the genetic code is degenerate (more than one codon can code for the same amino acid), a mixture of oligonucleotides is synthesized that contains all possible nucleotide sequences encoding the amino acid sequence of the tryptic fragment. These probes are radioactively labeled and employed to screen a bovine cDNA library as described below.

Poly(A) containing RNA is isolated by oligo(dT) cellulose chromatography from total RNA isolated from fetal bovine bone cells by the method of Gehron-Robey et al in *Current Advances in Skeletogenesis*, Elsevier Science Publishers (1985). The total RNA was obtained from Dr. Marian Young, National Institute of Dental Research, National Institutes of Health. A cDNA library is made in lambda gt10 (Toole et al supra) and plated on 50 plates at 8000 recombinants per plate. These recombinants (400,000) are screened on duplicate nitrocellulose filters with a combination of Probes 1, 2, 3, and 4 using the Tetramethylammonium chloride (TMAC) hybridization procedure [see Wozney et al *Science*, 242: 1528–1534 (1988)]. Twenty-eight positives are obtained and are replated for secondaries. Duplicate nitrocellulose replicas again are made. One set of filters are screened with Probes 1 and 2; the other with Probes 3 and 4. Six positives are obtained on the former, 21 positives with the latter. One of the six, called HEL5, is plaque purified, a phage plate stock made, and bacteriophage DNA isolated. This DNA is digested with EcoRI and subcloned into M13 and pSP65. The DNA sequence and derived amino acid sequence of this fragment is shown in Table I.

DNA sequence analysis of this fragment in M13 indicates that it encodes the desired tryptic peptide sequence set forth above, and this derived amino acid sequence is preceded by a basic residue (Lys) as predicted by the specificity of trypsin. The underlined portion of the sequence in Table I from amino acid #42 to #48 corresponds to the tryptic fragment identified above from which the oligonucleotide probes are designed. The derived amino acid sequence Ser-Gly-Ser-His-Gln-Asp-Ser-Ser-Arg as set forth in Table I from amino acid #15 to #23 is noted to be similar to a tryptic fragment sequence Ser-Thr-Pro-Ala-Gln-Asp-Val-Ser-Arg found in the 28,000–30,000 dalton purified bone preparation as described in the "BMP" co-pending applications mentioned above. This fragment set forth in Table I is a portion of the DNA sequence which encodes a bovine BMP-5 protein. The DNA sequence indicates an open reading frame from the 5' end of the clone of 420 base pairs, encoding a partial peptide of 140 amino acid residues (the first 7 nucleotides are of the adaptors used in the cloning procedure). An in-frame stop codon (TAA) indicates that this clone encodes the carboxy-terminal part of a bovine BMP-5 cartilage/bone protein.

124–amino acid #130 corresponds to the tryptic fragment identified above from which the oligonucleotide probes are designed.

The DNA sequence Of Table II indicates an open reading frame of 666 base pairs starting from the 5' end of the sequence of Table II, encoding a partial peptide of 222 amino acid residues. An in-frame stop codon (TGA) indicates that this clone encodes the carboxy-terminal part of a bovine BMP-6 protein of the invention. Based on knowledge of other BMP proteins and other proteins in the TGF-β family, it is predicted that the precursor polypeptide would be cleaved at the three basic residues (ArgArgArg) to yield a mature peptide beginning with residue 90 or 91 of the sequence of Table II.

TABLE I

| | |
|---|---|
| 1 TCTAGAGGTGAGAGCAGCCAACAAGAGAAAAAATCAAAACCGCAATAAATCCGGCTCTCAT<br>LeuGluValArgAlaAlaAsnLysArgLysAsnGlnAsnArgAsnLys<u>SerGlySerHis</u><br>(1)(15) | 61 |
| 62 GAGGACTCCTCTAGAATGTCCAGTGTTGGAGATTATAACACCAGTGAACAAAAACAAGCC<br><u>GlnAspSerSerArg</u>MetSerSerValGlyAspTyrAsnThrSerGluGlnLysGlnAla<br>(23) | 121 |
| 122 TGTAAAAAGCATGAACTCTATGTGAGTTTCCGGGATCTGGGATGGCAGGACTGGATTATA<br>CysLysLys<u>HisGluLeuTyrValSerPheArgAspLeuGlyTrpGlnAspTrpIleIle</u><br>(42) | 181 |
| 182 GCACCAGAAGGATATGCTGCATTTTATTGTGATGGAGAATGTTCTTTTCCACTCAATGCC<br>AlaProGluGlyTyrAlaAlaPheTryCysAspGlyGluCysSerPheProLeuAsnAla | 241 |
| 242 CATATGAATGCCACCAATCATGCCATAGTTCAGACTCTGGTTCACCTGATGTTTCCTGAC<br>HisMetAsnAlaThrAsnHisAlaIleValGlnThrLeuValHisLeuMetPheProAsp | 301 |
| 302 CACGTACCAAAGCCTTGCTGCGCGACAAACAAACTAAATGCCATCTCTGTGTTGTACTTT<br>HisValProLysProCysCysAlaThrAsnLysLeuAsnAlaIleSerValLeuTyrPhe | 361 |
| 362 GATGACAGCTCCAATGTCATTTTGAAAAAGTACAGAAATATGGTCGTGCGTTCGTGTGGT<br>AspAspSerSerAsnValIleLeuLysLysTyrArgAsnMetValValArgSerCysGly | 421 |
| 422 TGCCACTAATAGTGCATAATAATGGTAATAAGAAAAAAGATCTGTATGGAGGTTTATGA<br>CysHisEnd<br>(140) | 481 |
| 481 CTACAATAAAAAATATCTTTCGGATAAAAGGGGAATTTAATAAAATTAGTCTGGCTCATT | 540 |
| 541 TCATCTCTGTAACCTATGTACAAGAGCATGTATATAGT | 578 |

The remaining positive clones isolated with probes #1, #2, #3, and #4 described above are screened with HEL5 and a further clone is identified under reduced stringency conditions [5× SSC, 0.1% SDS, 5× Denhardt's, 100 μg/ml salmon sperm DNA standard hybridization buffer (SHB) at 65° C., wash in 2× SSC, 0.1% SDS at 65° C.]. This clone is plaque purified, a phage plate stock made and bacteriophage DNA isolated. The DNA sequence and derived amino acid sequence of a portion of this clone is shown in Table II. This sequence represents the DNA sequence encoding a BMP-6 cartilage/bone protein of the invention.

The first underlined portion of the sequence in Table II from amino acid #97–amino acid #105 Ser-Thr-Pro-Ala-Gln-Asp-Val-Ser-Arg corresponds to the tryptic fragment found in the 28,000–30,000 dalton purified bovine bone preparation (and its reduced form at approximately 18,000–20,000 dalton reduced form) as, described in the "BMP" co-pending applications mentioned above. The second underlined sequence in Table II from amino acid

TABLE II

| | | | | | | (1) | | 9 | | 18 | | 27 | | 36 | | 45 | | 54 |
|---|---|---|---|---|---|---|---|---|---|---|---|---|---|---|---|---|---|---|

| CTG Leu | GGC Gly | ACG Thr | CGT Arg | GCT Ala | GT Val | G TGG Trp | GCC Ala | TCA Ser | GAG Glu | GCG Ala | CTG Leu | TTT Phe | GAC Asp |
|---|---|---|---|---|---|---|---|---|---|---|---|---|---|

| ATC Ile | GCC Ala | ACC Thr | AGC Ser | AAC Asn | CTG Leu | TGG Trp | GCC Ala | CTG Leu | CCG Pro | CCG Pro | GGG Gly | ATG MET | GGG Gly |

Position: 63, 72, 81, 90, 99, 108

| CAG Gln | AGC Ser | GTG Val | GTC Val | ACG Thr | CGT Arg | GAT Asp | GTC Val | CTC Leu | ACT Thr | CAG Gln | CAC His | GCC Ala | GCG Ala |

Position: 117, 126, 135, 144, 153, 162

| CTG Leu | GGC Gly | AGG Arg | GAC Asp | GGC Gly | CGT Arg | TAC Tyr | AAG Lys | CTC Leu | AGC Ser | ATC Ile | CCT Pro | GGG Gly | GGC Gly |

Position: 171, 180, 189, 198, 207, 216

| AAG Lys | AGT Ser | GAG Glu | GTC Val | GGC Gly | CCC Pro | CGC Arg | CCC Pro | GTG Val | CAG Gln | CGG Arg | TTC Phe | TTC Phe | TTC Phe |

Position: 225, 234, 243, 252, 261, 270

| CAG Gln | GCC Ala | CGG Arg | AAC Asn | CGC Arg | TCC Ser | ACC Thr | CCG Pro | AGT Ser | AGC Ser | GCC Ala | GTG Val | CAG Gln | CGG Arg |

Position: 279, 288, 297, 306, 315, 324

| GCC Ala | TCA Ser | GAC Asp | TAC Tyr | AAC Asn | AGC Ser | (97) | GAG Glu | AGC Ser | CAG Gln | CCG Pro | AAG Lys | ACG Thr | TGC Cys |

Position: 333, 342, 351, 360, 369, 378

| | | | | | | | | | | | | | |
| --- | --- | --- | --- | --- | --- | --- | --- | --- | --- | --- | --- | --- | --- |
| | | | | | (121) | | (124) | | | | | | CTC Leu |

| TAC Tyr | AGC Ser | TTC Phe | CAG Gln | GAC Asp | CTG Leu | GGG Gly | CTG Leu | TGG Trp | GAC Asp | TCG Ser | ATC Ile | TGG Trp | CCC Pro |

Position: 387, 396, 405, 414, 423, 432

| TAC Tyr | GCC Ala | AAC Asn | TAC Tyr | TGT Cys | CGT Arg | GGA Gly | GAA Glu | TCG Ser | AGC Ser | CCT Pro | CTC Leu | TTC Phe | CAC His |

Position: 441, 450, 459, 468, 477, 486

| AAC Asn | ACC Thr | AAC Asn | CAT His | GCC Ala | ATC Ile | GTG Val | CAG Gln | CTG Leu | TCG Ser | CTG Leu | CAC His | GCA Ala | ATG MET |

Position: 495, 504, 513, 522, 531, 540

| CGT Ala | CGT Ala | ACC Thr | AAC Asn | AAC Asn | AAC Asn | GTG Val | CAG Gln | CTG Leu | GTT Val | ATG MET | CTC Leu | AAG Lys | GAG Glu |

TABLE II-continued

| | 549 | | | 558 | | | 567 | | | 576 | | | 585 | | | 594 |
|---|---|---|---|---|---|---|---|---|---|---|---|---|---|---|---|---|
| TAC Tyr | GTC Val | CCC Pro | AAA Lys | CCG Pro | TGC Cys | TGC Cys | GCG Ala | CCC Pro | ACG Thr | AAA Lys | CTG Leu | AAC Asn | GCC Ala | ATC Ile | TCG Ser | GTG Val | CTC Leu |

| | 603 | | | 612 | | | 621 | | | 630 | | | 639 | | | 648 |
|---|---|---|---|---|---|---|---|---|---|---|---|---|---|---|---|---|
| TAC Tyr | TTC Phe | GAC Asp | AAC Asn | TCC Ser | AAT Asn | GTC Val | ATC Ile | CTG Leu | AAG Lys | AAG Lys | TAC Tyr | CGG Arg | AAC Asn | ATG MET | GTC Val | GTA Val |

| | | | | 657 | | | | | | 666 | | | | | | 676 | | | | | | 686 | | | | | | 696 | | | | | 706 | | | | 716 |
|---|---|---|---|---|---|---|---|---|---|---|---|---|---|---|---|---|---|---|---|---|---|---|---|---|---|---|---|---|---|---|---|---|---|---|---|---|---|
| CGA Arg | GCG Ala | TGT Cys | GGG Gly | TGC Cys | | | | | | CAC His (222) | | | | | | TGACTCGGGG | | | | | | TGAGTGCGTG | | | | | | GGGACCGTGT | | | | | GCACACTG | | | | CCTGGACTCC |

726 TGGATCACGT

736 CCGCCTTAAG

746 CCCACAGAGG

756 CCCCCGGGAC

766 ACAGGAGGAG

776 ACCCCGAGGC

786 CACCTTCGGC

796 TGGCGTTGGC

806 CTTTCCGCCC

816 AACGCAGACC

826 CGAAGGGACC

836 CTGTCCGCCC

846 CTTGCTCACA

856 CCGTGAGCGT

866 TGTGAGTAGC

876 CATCGGGCTC

886 TAGGAAGCAG

CACTCGAG

EXAMPLE V Human BMP-6 Proteins

Human cell lines which synthesize BMP-5 and/or BMP-6 mRNAs are identified in the following manner. RNA is isolated from a variety of human cell lines, selected for poly(A)-containing RNA by chromatography on oligo(dT) cellulose, electrophoresed on a formaldehyde-agarose gel, and transferred to nitrocellulose. A nitrocellulose replica of the gel is hybridized to a single standed M13 $^{32}$P-labeled probe corresponding to the above mentioned BMP-5 EcoRI-BglII fragment containing nucleotides 1–465 of the sequence of Table I. A strongly hybridizing band is detected in the lane corresponding to the human osteosarcoma cell line U-2OS RNA. Another nitrocellulose replica is hybridized to a single stranded M13 $^{32}$P-labeled probe containing the PstI-SmaI fragment of bovine BMP-6 (corresponding to nucleotides 106–261 of Table II). It is found that several RNA species in the lane corresponding to U-2OS RNA hybridize to this probe.

A cDNA Library is made in the vector lambda ZAP (Stratagene) from U-20S poly(A) -containing RNA using established techniques (Toole et al.). 750,000 recombinants of this library are plated and duplicate nitrocellulose replicas made. The SmaI fragment of bovine BMP-6 corresponding to nucleotides 259–751 of Table II is labeled by nick-translation and hybridized to both sets of filters in SHB at 65°. One set of filters is washed under stringent conditions (0.2× SSC, 0.1% SDS at 65°), the other under reduced stringency conditions (1× SSC, 0.1% SDS at 65°). Many duplicate hybridizing recombinants (approximately 162) are noted. 24 are picked and replated for secondaries. Three nitrocellulose replicas are made of each plate. One is hybridized to the BMP-6 SmaI probe, one to a nick-translated BMP-6 PstI-SacI fragment (nucleotides 106–378 of Table II), and the third to the nick-translated BMP-5 XbaI fragment (nucleotides 1–76 of Table I). Hybridization and washes are carried out under stringent conditions.

Six clones which hybridize to the second probe more strongly than to the third are picked and transformed into plasmids. Restriction mapping, Southern blot analysis, and DNA sequence analysis of these plasmids indicate that there are two classes of clones. Clones U2-7 and U2-10 contain human BMP-6 coding sequence based on their stronger hybridization to the second probe and closer DNA homology to the bovine BMP-6 sequence of Table II than the other 4 clones. DNA sequence data derived from these clones indicates that they encode a partial polypeptide of 132 amino acids comprising the carboxy-terminus of the human BMP-6 protein. U2-7 was deposited with the American Type Culture Collection (ATCC), Rockville, Md. on Jun. 23, 1989 under accession number 68021.

A primer extended cDNA library is made from U-2 OS mRNA using the oligonucleotide GGAATCCAAGGCA-GAATGTG, the sequence being based on the 3' untranslated sequence of the human BMP-6 derived from the clone U2-10. This library is screened with an oligonucleotide of the sequence CAGAGTCGTAATCGC, derived from the BMP-6 coding sequence of U2-7 and U2-10. Hybridization is in standard hybridization buffer (SHB) at 42 degrees centigrade, with wash conditions of 42 degrees centigrade, 5× SSC, 0.1% SDS. Positively hybridizing clones are isolated. The DNA insert of one of these clones, PEH6-2, indicates that it extends further in a 5' direction than either U2-7 or U-2-10. A primer extended cDNA library constructed from U-20S mRNA as above is screened with an oligonucleotide of the sequence GCCTCTCCCCTC-CGACGCCCCGTCCTCGT, derived from the sequence near the 5' end of PEH6-2. Hybridization is at 65 degrees centigrade in SHB, with washing at 65 degrees centigrade in 2× SSC, 0.1% SDS. Positively hybridizing recombinants are isolated and analyzed by restriction mapping and DNA sequence analysis.

The 5' sequence of the insert of one of the positively hybridizing recombinants, PE5834#7, is used to design an oligonucleotide of the sequence CTGCTGCTCCTCCT-GCTGCCGGAGCGC. A random primed cDNA library [synthesized as for an oligo (dT) primed library except that (dN)$_6$ is used as the primer] is screened with this oligonucleotide by hybridization at 65 degrees centigrade in SHB with washing at 65 degrees centigrade in 2× SSC, 0.1% SDS. A positively hybridizing clone, RP10, is identified, isolated, and the DNA sequence sequence from the 5' end of its insert is determined. This sequence is used to design an oligonucleotide of the sequence TCGGGCTTCCTGTACCG-GCGGCTCAAGACGCAGGAGAAGCGGGAGATGCA.

A human placenta cDNA library (Stratagene catalog #936203) is screened with this oligonucleotide by hybridization in SHB at 65 degrees centigrade, and washing at 65 degrees centigrade with 0.2× SSC, 0.1% SDS. A positively hybridizing recombinant designated BMP6C35 is isolated. DNA sequence analysis of the insert of this recombinant indicates that it encodes the complete human BMP-6 protein. BMP6C35 was deposited with the American Type Culture Collection, 12301 Parklawn Drive, Rockville, Md. USA on Mar. 1, 1990 under Accession Number 68245.

The DNA and derived amino acid sequence of the majority of the insert of BMP6C35 is given in Table III. This DNA sequence contains an open reading frame of 1539 base pairs which encodes the 513 amino acid human BMP-6 protein precursor. The presumed initiator methionine codon is preceded by a 5'untranslated sequence of 159 base pairs with stop codons in all three reading frames. The stop codon at nucleotides 1699–1701 is followed by at least 1222 base pairs of 3'untranslated sequence. It is noted that U2-7 has a C residue at the position corresponding to the T residue at position 1221 of BMP6C35; U2-7 also has a C residue at the position corresponding to the G residue at position 1253 of BMP6C35. These do not cause amino acid differences in the encoded proteins, and presumably represent allelic variations.

The oligonucleotide TCGGGCTTCCTGTACCGGCG-GCTCAAGACGCAGGAGAAGCGGGAGATGCA is used to screen a human genomic library (Toole et al supra), by hybridizing nitrocellulose replicas of 1×10$^6$ recombinants with the oligonucleotide in SHB at 65 degrees centigrade, and washing at 65 degrees centigrade with 0.2× SSC, 0.1% SDS. Positively hybridizing clones are purified. The oligonucleotide hybridizing region is localized to an approximately 1.5 kb Pst I fragment. DNA sequence analysis of this fragment confirms the 5' sequence indicated in Table III.

The DNA sequence of the human BMP-6 clone set forth in Table III reveals an open reading frame of 1539 bp encoding a protein of 513 amino acids. The first underlined portion of the sequence in Table III from amino acid #388 to #396, Ser-Thr-Gln-Ser-Gln-Asp-Val-Ala-Arg, corresponds to the similar sequence Ser-Thr-Pro-Ala-Gln-Asp-Val-Ser-Arg of the bovine sequence described above and set forth in Table II. The second underlined sequence in Table III from amino acid #415 through #421 His-Glu-Leu-Tyr-Val-Ser-Phe, corresponds to the tryptic fragment identified above from which the oligonucleotide probes are designed. When the tryptic sequence His-Glu-Leu-Tyr-Val-Ser-Phe-(Ser) described above was identified, it was noted to be similar to a sequence found in other BMP proteins for example the sequence His-Pro-Leu-Tyr-Val-Asp-Phe-Ser found in the bovine and human cartilage/bone protein BMP-2A sequence as described in co-pending U.S. application Ser. No. 179,100. BMP-6 therefore represents a new member of the BMP subfamily of TGF-β like molecules which includes the molecules BMP-2 (also sometimes referred to as BMP-2A or BMP-2 Class I), 3, 4 (also sometimes referred to as BMP-2B or BMP-2 Class II), 5 and 7 described in co-pending applications cited above.

Based on knowledge of other BMP proteins, as well as other proteins in the TGF-β family, BMP-6 is predicted to be synthesized as a precursor molecule and the precursor polypeptide would be cleaved between amino acid #381 and amino acid #382 yielding a 132 amino acid mature polypeptide with a calculated molecular weight of approximately 15 Kd. The mature form of BMP-6 contains three potential N-linked glycosylation sites per polypeptide chain.

It is contemplated that the active BMP-6 protein molecule is a dimer. It is further contemplated that the processing of BMP-6 into the mature form involves dimerization and removal of the N-terminal region in a manner analogous to the processing of the related protein TGF-β [L. E. Gentry, et al., *Molec. & Cell. Biol.* 8:4162 (1988); R. Dernyck, et al., *Nature* 316:701 (1985)].

TABLE III

| 10 CGACCATGAG | | 20 AGATAAGGAC | | | 30 TGAGGGCCAG | | | 40 GAAGGGGAAG | | | 50 CGAGCCCGCC | | | |
|---|---|---|---|---|---|---|---|---|---|---|---|---|---|---|
| 60 GAGAGGTGGC | | 70 GGGGACTGCT | | | 80 CACGCCAAGG | | | 90 GCCACAGCGG | | | 100 CCGCCGTCCG | | | |
| 110 GCCTCGCTCC | | 120 GCCCGTCCAC | | | 130 GCCTCGCGGG | | | 140 ATCCGCGGGG | | | 150 GCAGCCCGGC | | | |
| 159 CGGGCGGG | | ATG MET (1) | CCG Pro | 168 GGG Gly | CTG Leu | GGG Gly | 177 CGG Arg | AGG Arg | GCG Ala | 186 CAG Gln | TGG Trp | CTG Leu | 195 TGC Cys | |
| TGG Trp | TGG Trp | 204 TGG Trp | GGG Gly | CTG Leu | 213 CTG Leu | TGC Cys | AGC Ser | 222 TGC Cys | TGC Cys | GGG Gly | 231 CCC Pro | CCG Pro | CCG Pro | 240 CTG Leu |
| CGG Arg | CCG Pro | 249 CCC Pro | TTG Leu | CCC Pro | 258 CGT Ala | GCC Ala | GCG Ala | 267 GCC Ala | GCC Ala | GCC Ala | 276 GCC Ala | GGG Gly | GGG Gly | 285 CAG Gln |
| CTG Leu | CTG Leu | 294 GGG Gly | GAC Asp | GGC Gly | 303 GGG Gly | AGC Ser | CCC Pro | 312 GGC Gly | CGC Arg | ACG Thr | 321 GAG Glu | CAG Gln | CCG Pro | 330 CCG Pro |
| CCG Pro | TCG Ser | 339 CCG Pro | CAG Gln | TCC Ser | 348 TCC Ser | TCG Ser | GGC Gly | 357 TTC Phe | CTG Leu | TAC Tyr | 366 CGG Arg | CGG Arg | CTC Leu | 375 AAG Lys |
| ACG Thr | CAG Gln | 384 GAG Glu | AAG Lys | CGG Arg | 393 GAG Glu | ATG MET | CAG Gln | 402 AAG Lys | GAG Glu | ATC Ile | 411 TTG Leu | TCG Ser | GTG Val | 420 CTG Leu |
| GGG Gly | CTC Leu | 429 CCG Pro | CAC His | CGG Arg | 438 CCC Pro | CGG Arg | CCC Pro | 447 CTG Leu | CAC His | GGC Gly | 456 CTC Leu | CAA Gln | CAG Gln | 465 CCG Pro |
| CAG Gln | CCC Pro | 474 CCG Pro | GCG Ala | CTC Leu | 483 CGG Arg | CAG Gln | CAG Gln | 492 GAG Glu | GAG Glu | CAG Gln | 501 CAG Gln | CAG Gln | CAG Gln | 510 CAG Gln |
| CAG Gln | CTG Leu | 519 CCT Pro | CGC Arg | GGA Gly | 528 GAG Glu | CCC Pro | CCT Pro | 537 CCC Pro | GGG Gly | CGA Arg | 546 CTG Leu | AAG Lys | TCC Ser | 555 GCG Ala |
| CCC Pro | CTC Leu | 564 TTC Phe | ATG MET | CTG Leu | 573 GAT Asp | CTG Leu | TAC Tyr | 582 AAC Asn | GCC Ala | CTG Leu | 591 TCC Ser | GCC Ala | GAC Asp | 600 AAC Asn |
| GAC Asp | GAG Glu | 609 GAC Asp | GGG Gly | GCG Ala | 618 TCG Ser | GAG Glu | GGG Gly | 627 GAG Glu | AGG Arg | CAG Gln | 636 CAG Gln | TCC Ser | TGG Trp | 645 CCC Pro |
| CAC His | GAA Glu | 654 GCA Ala | GCC Ala | AGC Ser | 663 TCG Ser | TCC Ser | CAG Gln | 672 CGT Arg | CGG Arg | CAG Gln | 681 CCG Pro | CCC Pro | CCG Pro | 690 GGC Gly |
| GCC Pro | GCG Pro | 699 CAC Gly | CCG Ala | CTC Ala | 708 AAC His | CGC Pro | AAG Leu | 717 AGC Asn | CTT Arg | CTG Lys | 726 GCC Ser | CCC Leu | GGA Leu | 735 TCT Ala |
| | | 744 | | | 753 | | | 762 | | | 771 | | | 780 |

TABLE III-continued

| | | | | | | | | | | | | | | |
|---|---|---|---|---|---|---|---|---|---|---|---|---|---|---|
| GGC | AGC | GGC | GGC | GCG | TCC | CCA | CTG | ACC | AGC | GCG | CAG | GAC | AGC | GCC |
| Gly | Ser | Gly | Gly | Ala | Ser | Pro | Leu | Thr | Ser | Ala | Gln | Asp | Ser | Ala |
| | | 789 | | | 798 | | | 807 | | | 816 | | | 825 |
| TTC | CTC | AAC | GAC | GCG | GAC | ATG | GTC | ATG | AGC | TTT | GTG | AAC | CTG | GTG |
| Phe | Leu | Asn | Asp | Ala | Asp | MET | Val | MET | Ser | Phe | Val | Asn | Leu | Val |
| | | 834 | | | 843 | | | 852 | | | 861 | | | 870 |
| GAG | TAC | GAC | AAG | GAG | TTC | TCC | CCT | CGT | CAG | CGA | CAC | CAC | AAA | GAG |
| Glu | Tyr | Asp | Lys | Glu | Phe | Ser | Pro | Arg | Gln | Arg | His | His | Lys | Glu |
| | | 879 | | | 888 | | | 897 | | | 906 | | | 915 |
| TTC | AAG | TTC | AAC | TTA | TCC | CAG | ATT | CCT | GAG | GGT | GAG | GTG | GTG | ACG |
| Phe | Lys | Phe | Asn | Leu | Ser | Gln | Ile | Pro | Glu | Gly | Glu | Val | Val | Thr |
| | | 924 | | | 933 | | | 942 | | | 951 | | | 960 |
| CGT | GCA | GAA | TTC | CGC | ATC | TAC | AAG | GAC | TGT | GTT | ATG | GGG | AGT | TTT |
| Phe | Arg | Ile | Tyr | Lys | Asp | Cys | Val | MET | Ala | Ala | Glu | Gly | Ser | Phe |
| | | 969 | | | 978 | | | 987 | | | 996 | | | 1005 |
| AAA | AAC | CAA | ACT | TTT | CTT | ATC | AGC | ATT | TAT | CAA | GTC | TTA | CAG | GAG |
| Lys | Asn | Gln | Thr | Phe | Leu | Ile | Ser | Ile | Tyr | Gln | Val | Leu | Gln | Glu |
| | | 1014 | | | 1023 | | | 1032 | | | 1041 | | | 1050 |
| CAT | CAG | CAC | AGA | GAC | TCT | GAC | CTG | TTT | TTG | TTG | GAC | ACC | CGT | GTA |
| His | Gln | His | Arg | Asp | Ser | Asp | Leu | Phe | Leu | Leu | Asp | Thr | Arg | Val |
| | | 1059 | | | 1068 | | | 1077 | | | 1086 | | | 1095 |
| GTA | TGG | GCC | TCA | GAA | GAA | GGC | TGG | CTG | GAA | TTT | GAC | ATC | ACG | GCC |
| Val | Trp | Ala | Ser | Glu | Glu | Gly | Trp | Leu | Glu | Phe | Asp | Ile | Thr | Ala |
| | | 1104 | | | 1113 | | | 1122 | | | 1131 | | | 1140 |
| ACT | AGC | AAT | CTG | TGG | GTT | GTG | ACT | CCA | CAG | CAT | AAC | ATG | GGG | CTT |
| Thr | Ser | Asn | Leu | Trp | Val | Val | Thr | Pro | Gln | His | Asn | MET | Gly | Leu |
| | | 1149 | | | 3158 | | | 1167 | | | 1176 | | | 1185 |
| CAG | CTG | AGC | GTG | GTG | ACA | AGG | GAT | GGA | GTC | CAC | GTC | CAC | CCC | CGA |
| Gln | Leu | Ser | Val | Val | Thr | Arg | Asp | Gly | Val | His | Val | His | Pro | Arg |
| | | 1194 | | | 1203 | | | 1212 | | | 1221 | | | 1230 |
| GCC | GCA | GGC | CTG | GTG | GGC | AGA | GAC | GGC | CCT | TAC | GAT | AAG | CAG | CCC |
| Ala | Ala | Gly | Leu | Val | Gly | Arg | Asp | Gly | Pro | Tyr | Asp | Lys | Gln | Pro |
| | | 1239 | | | 1248 | | | 1257 | | | 1266 | | | 1275 |
| TTC | ATG | GTG | CGT | TTC | TTC | AAA | GTG | AGT | GAG | GTC | CAC | GTG | CGC | ACC |
| Phe | MET | Val | Ala | Phe | Phe | Lys | Val | Ser | Glu | Val | His | Val | Arg | Thr |
| | | 1284 | | | 1293 | | | 1302 | | | 1311 | | | 1320 |
| ACC | AGG | TCA | GCC | TCC | AGC | CGA | CGC | CAA | CAG | CGT | AAT | CGC | | |
| Thr | Arg | Ser | Ala | Ser | Ser | Arg | Arg | Arg | | | | | | |
| | | | | | | | | Gln | Gln | Ser | Arg | Asn | Arg | |
| | | | | | | | | (382) | | | | | | |
| | | 1329 | | | 1338 | | | 1347 | | | 1356 | | | 1365 |
| TCT | ACC | CAG | TCC | CAG | GAC | GTG | GCG | CGG | GTC | TCC | AGT | CGT | TCA | GAT |
| Ser | Thr | Gln | Ser | Gln | Asy | Val | Ala | Arg | Val | Ser | Ser | Ala | Ser | Asp |
| (388) | | | | | | | | | | | | | | |
| | | 1374 | | | 1383 | | | 1392 | | | 1401 | | | 1410 |
| TAC | AAC | AGC | AGT | GAA | TTG | AAA | ACA | GCC | TGC | AGG | AAG | CAT | GAG | CTG |
| Tyr | Asn | Ser | Ser | Glu | Leu | Lys | Thr | Ala | Cys | Arg | Lys | His | Glu | Leu |
| | | | | | | | | (412) | | | | | | |
| | | 1419 | | | 1428 | | | 1437 | | | 1446 | | | 1455 |
| TAT | GTG | AGT | TTC | CAA | GAC | CTG | GGA | CAG | GAC | TGG | ATC | ATT | GCA | |
| Tyr | Val | Ser | Phe | Gln | Asp | Leu | Gly | Trp | Gln | Asp | Trp | Ile | Ile | Ala |
| | | 1464 | | | 1473 | | | 1482 | | | 1491 | | | 1500 |
| CCC | AAG | GGC | TAT | CGT | GCC | AAT | TAC | TGT | GAT | GGA | GAA | TGC | TCC | TTC |
| Pro | Lys | Gly | Tyr | Ala | Ala | Asn | Tyr | Cys | Asp | Gly | Glu | Cys | Ser | Phe |
| | | 1509 | | | 1518 | | | 1527 | | | 1536 | | | 1545 |
| CCA | CTC | AAC | GCA | CAC | ATG | AAT | GCA | ACC | AAC | CAC | GCG | ATT | GTG | CAG |
| Pro | Leu | Asn | Ala | His | MET | Asn | Ala | Thr | Asn | His | Ala | Ile | Val | Gln |
| | | 1554 | | | 1563 | | | 1572 | | | 1581 | | | 1590 |
| ACC | TTG | GTT | CAC | CTT | ATG | AAC | CCC | GAG | TAT | GTC | CCC | AAA | CCG | TGC |

TABLE III-continued

| Thr | Leu | Val | His | Leu | MET | Asn | Pro | Glu | Tyr | Val | Pro | Lys | Pro | Cys |
|---|---|---|---|---|---|---|---|---|---|---|---|---|---|---|
| TGT | GCG | 1599 CCA | ACT | AAG | 1608 CTA | AAT | GCC | 1617 ATC | TCG | GTT | 1626 CTT | TAC | TTT | 1635 GAT |
| Cys | Ala | Pro | Thr | Lys | Leu | Asn | Ala | Ile | Ser | Val | Leu | Tyr | Phe | Asp |
| GAC | AAC | 1644 TCC | AAT | GTC | 1653 ATT | CTG | AAA | 1662 AAA | TAC | AGG | 1671 AAT | ATG | GTT | 1680 GTA |
| Asp | Asn | Ser | Asn | Val | Ile | Leu | Lys | Lys | Tyr | Arg | Asn | MET | Val | Val |
| AGA | CGT | 1689 TGT | GGA | TGC | 1698 CAC | 1708 TAACTCGAAA | | 1718 CCAGATGCTG | | | 1728 GGGACACACA | | | |
| Arg | Ala | Cys | Gly | Cys | His (513) | | | | | | | | | |

| 1738 TTCTGCCTTG | 1748 GATTCCTAGA | 1758 TTACATCTGC | 1768 CTTAAAAAAA | 1778 CACGGAAGCA |
|---|---|---|---|---|
| 1788 CAGTTGGAGG | 1798 TGGGACGATG | 1808 AGACTTTGAA | 1818 ACTATCTCAT | 1828 GCCAGTGCCT |
| 1838 TATTACCCAG | 1848 GAAGATTTTA | 1858 AAGGACCTCA | 1868 TTAATAATTT | 1878 CGTCACTTGG |
| 1888 TAAATGACGT | 1898 GAGTAGTTGT | 1908 TGGTCTGTAG | 1918 CAAGCTGAGT | 1928 TTGGATGTCT |
| 1938 GTAGCATAAG | 1948 GTCTGGTAAC | 1958 TGCAGAAACA | 1968 TAACCGTGAA | 1978 CGTCTTCCTA |
| 1988 CCCTCCTCCC | 1998 CCAAAAACCC | 2008 ACCAAAATTA | 2018 GTTTTAGCTG | 2028 TAGATCAAGC |
| 2038 TATTTGGGGT | 2048 GTTTGTTAGT | 2058 AAATAGGGAA | 2068 AATAATCTCA | 2078 AAGGAGTTAA |
| 2088 ATGTATTCTT | 2098 GGCTAAAGGA | 2108 TCAGCTGGTT | 2118 CAGTACTGTC | 2128 TATCAAAGGT |
| 2138 AGATTTTACA | 2148 GAGAACAGAA | 2158 ATCGGGGAAG | 2168 TGGGGGGAAC | 2178 GCCTCTGTTC |
| 2188 AGTTCATTCC | 2198 CAGAAGTCCA | 2208 CAGGACGCAC | 2218 AGCCCAGGCC | 2228 ACAGCCAGGG |
| 2238 CTCCACGGGG | 2248 CGCCCTTGTC | 2258 TCAGTCATTG | 2268 CTGTTGTATG | 2278 TTCGTGCTGG |
| 2288 AGTTTGTTG | 2298 GTGTGAAAAT | 2308 ACACTTATTT | 2318 CAGCCAAAAC | 2328 ATACCATTTC |
| 2338 TACACCTCAA | 2348 TCCTCCATTT | 2358 CGTGTACTCT | 2368 TTGCTAGTAC | 2378 CAAAAGTAGA |
| 2388 CTGATTACAC | 2398 TGAGGTGAGG | 2408 CTACAAGGGG | 2418 TGTGTAACCG | 2428 TGTAACACGT |
| 2438 GAAGGCAGTG | 2448 CTCACCTCTT | 2458 CTTTACCAGA | 2468 ACGGTTCTTT | 2478 GACCAGCACA |
| 2488 TTAACTTCTG | 2498 GACTGCCGGC | 2508 TCTAGTACCT | 2518 TTTCAGTAAA | 2528 GTGGTTCTCT |
| 2538 GCCTTTTTAC | 2548 TATACAGCAT | 2558 ACCACGCCAC | 2568 AGGGTTAGAA | 2578 CCAACGAAGA |
| 2588 AAATAAAATG | 2598 AGGGTGCCCA | 2608 CGTTATAAGA | 2618 ATGGTGTTAG | 2628 GGGGATGAGC |
| 2638 ATGCTGTTTA | 2648 TGAACGGAAA | 2658 TCATGATTTC | 2668 CCTGTAGAAA | 2678 GTGAGGCTCA |
| 2688 GATTAAATTT | 2698 TAGAATATTT | 2708 TCTAAATGTC | 2718 TTTTTCACAA | 2728 TCATGTGACT |
| 2738 GGGAAGGCAA | 2748 TTTCATACTA | 2758 AACTGATTAA | 2768 ATAATACATT | 2778 TATAATCTAC |
| 2788 | 2798 | 2808 | 2818 | 2828 |

TABLE III-continued

| | | | | |
|---|---|---|---|---|
| AACTGTTTGC | ACTTACAGCT | TTTTTTGTAA | ATATAAACTA | TAATTTATTG |
| 2838<br>TCTATTTTAT | 2848<br>ATCTGTTTTG | 2858<br>CTGTGGCGTT | 2868<br>GGGGGGGGGG | 2878<br>CCGGGCTTTT |
| 2888<br>GGGGGGGGGG | 2898<br>GTTTGTTTGG | 2908<br>GGGGTGTCGT | 2918<br>GGTGTGGGCG | GGCGG |

Comparision of the sequence of murine Vgr-1 [Lyons, et al., *PNAS* 86:4554 (1989)] to human BMP-6 reveals a degree of amino acid sequence identity greater than 92% The murine Vgr-1 is likely the murine homologue of BMP-6. Human BMP-6 shares homology with other BMP molecules as well as other members of the. TGF-β superfamily of molecules. The cysteine-rich carboxy-terminal 102 amino acid residues of human BMP-6 shares the following homologies with BMP proteins disclosed in copending applications described above: 61% identity with BMP-2; 44% identity with BMP-3, 60% identity with BMP-4; 91% identity with BMP-5; and 87% identity with BMP-7. Human BMP-6 further shares the following homologies: 41% identity with TGF-β3; 39% identity with TGF-β2; 37% identity with TGF-β1; 26% identity with Mullerian Inhibiting Substance (MIS), a testicular glycoprotein that causes regression of the Mullerian duct during development of the male embryo; 25% identity with inhibin α; 43% identity with inhibin $β_B$; 49% identity with inhibin $β_A$; 58% identity with Vgl, a Xenopus factor which may be involved in mesoderm induction in early embryogenesis (Weeks and Melton, *Cell* 51:861–867(1987)]; and 59% identity with Dpp the product of the Drosophila decapentaplegic locus which is required for dorsal-ventral specification in early embryogenesis and is involved in various other developmental processes at later stages of development [Padgett, et al., *Nature* 325:81–84 (1987)].

The procedures described above and additional methods known to those skilled in the art may be employed to isolate other related proteins of interest by utilizing the bovine or human proteins as a probe source. Such other proteins may find similar utility in, inter alia, fracture repair, wound healing and tissue repair.

Additional methods known to those skilled in the art may be used to isolate the genetic material encoding human and other species' cartilage/bone proteins of the invention.

EXAMPLE VI

Expression of the BMP-6 Proteins

In order to produce bovine, human or other mammalian proteins of the invention, the DNA encoding it is transferred into an appropriate expression vector and introduced into mammalian cells or other preferred eukaryotic or prokaryotic hosts by conventional genetic engineering techniques. It is contemplated that the preferred expression system for biologically active recombinant human proteins of the invention will be stably transformed mammalian cells. It is further contemplated that the preferred mammalian cells will be CHO cells. The transformed host cell is cultured and the BMP-6 proteins expressed thereby are recovered and purified. The recombinantly expressed BMP-6 proteins are free of proteinaceous materials with which they ordinarily are associated in nature and are purified from other proteinaceous materials with which they are co-produced as well as from other contaminants, such as materials found in the culture media.

In order to express biologically active human BMP-6 proteins, a selected host cell is transformed, using techniques known to those skilled in the art of genetic engineering, with a DNA sequence encoding human BMP-6 protein. The DNA encoding BMP-6 comprises nucleotide #1393 to #1698 set forth in Table III encoding amino acid #412 to #513. The transformed host cells are cultured and the BMP-6 protein comprising amino acid #412 to amino acid #513 as set forth in Table III is expressed. The expressed protein is recovered, isolated and purified form the culture and culture medium. The purified protein is substantially free from other proteinaceous materials with which it is co-produced as well as from other contaminants. In other embodiments, the DNA sequence utilized in expressing human BMP-6 proteins of the invention comprise the longer nucleotide sequence comprising nucleotide #1321 to #1698 encoding the amino acid sequence comprising #388 to #513. In further embodiment the DNA sequence utilized in expression comprises nucleotide #1303 to 1698 encoding the amino acid sequence comprising amino acid 382 to #513.

Expression in CHO cells for instance any comprise transformation of the host cell with a vector containing a DNA sequence comprising nucleotides #160 through #1712 of Table III. The transformed host cell is cultured and the expressed BMP-6 proteins are recovered and purified. It is contemplated that the recovered and purified BMP-6 protein comprises what is expected to be the mature form comprising amino acid #382–513. However, other forms of BMP-6 may be recovered and purified. These forms include proteins comprising amino acid #388–#513 and proteins comprising amino acid #412 to #513 as set forth in Table III.

One skilled in the art can construct mammalian expression vectors by employing the DNA sequences of the invention sequences and known vectors, such as pCD [Okayama et al., *Mol. Cell Biol.*, 2:161–170 (1982)] and pJL3, pJL4 [Gough et al., *EMBO J.*, 4:645–653 (1985)]. The transformation of these vectors into appropriate host cells may result in expression of the proteins of the invention.

One skilled in the art could manipulate the sequences of the invention by eliminating or replacing the mammalian regulatory sequences flanking the coding sequence with bacterial sequences to create bacterial vectors for intracellular or extracellular expression by bacterial cells. The coding sequences could be further manipulated, for example, ligated to other known linkers or modified by deleting non-coding sequences there-from or altering nucleotides therein by other known techniques. The modified coding sequence could then be inserted into a known bacterial vector using procedures such as described in T. Taniguchi et al., *Proc. Natl Acad. Sci. USA*, 77:5230–5233 (1980). This exemplary bacterial vector could then be transformed into bacterial host cells and a protein of the invention expressed thereby. For a strategy for producing extracellular expression of a cartilage and/or bone protein of the invention in bacterial cells., see, e.g. European patent application EPA 177,343.

Similar manipulations can be performed for the construction of an insect vector [See, e.g. procedures described in published European patent application 155,476] for expression in insect cells. A yeast vector could also be constructed employing yeast regulatory sequences for intracellular or extracellular expression of the factors of the present invention by yeast cells. [See, e.g., procedures described in published PCT application WO86/00639 and European patent application EPA 123,289].

A method for producing high levels of a protein of the invention from mammalian cells involves the construction of cells containing multiple copies of the heterologous gene encoding proteins of the invention. The heterologous gene may be linked to an amplifiable marker, e.g. the dihydrofolate reductase (DHFR) gene for which cells containing increased, gene copies can be selected for propagation in increasing concentrations of methotrexate (MTX) according to the procedures of Kaufman and Sharp, *J. Mol. Biol.*, 159:601–629 (1982). This approach can be employed with a number of different cell types.

For example, a plasmid containing a DNA sequence for a protein of the invention in operative association with other plasmid sequences enabling expression thereof and the DHFR expression plasmid pAdA26SV(A)3 [Kaufman and Sharp, *Mol. Cell. Biol.*, 2:1304 (1982)] may be co-introduced into DHFR-deficient CHO cells, DUKX-BII, by calcium phosphate coprecipitation and transfection, electroperation or protoplast fusion. DHFR expressing transformants are selected for growth in alpha media with dialyzed fetal calf serum, and subsequently selected for amplification by growth in increasing concentrations of MTX (sequential steps in 0.02, 0.2, 1.0 and 5 uM MTX) as described in Kaufman et al., *Mol Cell Biol.*, 5:1750 (1983). Protein expression should increase with increasing levels of MTX resistance.

Transformants are cloned, and the proteins of the invention are recovered, isolated, and purified from the culture medium. Biologically active protein expression is monitored by the Rosen-modified Sampath-Reddi rat bone formation assay described above in Example III. Similar procedures can be followed to produce other related proteins.

EXAMPLE VII

Biological Activity of Expressed BMP-6 Proteins

To measure the biological activity of the expressed proteins obtained in Example VI above, the BMP-6 proteins are recovered from the culture media and purified. BMP-6 may be partially purified on a Heparin Sepharose column. 4 ml of the collected post transfection conditioned medium supernatant from one 100 mm culture dish is concentrated approximately 10 fold by ultrafiltration on a YM 10 membrane and then dialyzed against 20 mM Tris, 0.15M NaCl, pH 7.4 (starting buffer). This material is then applied to a 1.1 ml Heparin Sepharose column in starting buffer. Unbound proteins are removed by,an 8 ml wash of starting buffer, and bound proteins, including proteins of the invention, are desorbed by a 3–4 ml Wash of 20 mM Tris, 2.0M NaCl, pH 7.4.

The proteins bound by the Heparin column are concentrated approximately 10-fold on a Centricon 10 and the salt reduced by diafiltration with 0.1% trifluoroacetic acid. The appropriate amount of this solution is mixed with 20 mg of rat matrix and then assayed for in vivo bone and/or cartilage formation activity by the Rosen-modified Sampath-Reddi assay. A mock transfection supernatant fractionation is used as a control.

The implants containing rat matrix to which specific amounts of human BMP-6 proteins of the invention have been added are removed from rats after seven days and processed for histological evaluation. Representative sections from each implant are stained for the presence of new bone mineral with von Kossa and acid fuschin, and for the presence of cartilage-specific matrix formation using toluidine blue. The types of cells present within the section, as well as the extent to which these cells display phenotype are evaluated and scored as described in Example III.

Levels of activity may also be tested for host cell extracts. Partial purification is accomplished in a similar manner as described above except that 6M urea is included in all the buffers.

The foregoing descriptions detail presently preferred embodiments of the present invention. Numerous modifications and variations in practice thereof are expected to occur to those skilled in the art upon consideration of these descriptions. Those modifications and variations are believed to be encompassed within the claims appended hereto.

What is claimed is:

1. A composition comprising a purified human BMP-6 protein having the amino acid sequence set forth in FIG. 3 or a biologically active fragment thereof wherein said fragment is capable of inducing bone and/or cartilage formation in the Rosen-modified Sampath-Reddi assay.

2. The composition of claim 2 wherein said amino acid sequence comprises amino acid #412 to amino acid #513 of FIG. 3.

3. The composition of claim 2 wherein said amino acid sequence comprises amino acid #388 to amino acid #513 of FIG. 3.

4. The composition of claim 2 wherein said amino acid sequence comprises amino acid #382 to amino acid #513 of FIG. 3.

5. The composition of claim 2 further comprising a pharmaceutically acceptable matrix.

6. The composition of claim 6 wherein said matrix comprises a material selected from the group consisting of hydroxyapatite, collagen, polylactic acid and tricalcium phosphate.

7. A composition comprising a purified human BMP-6 protein produced by the steps of (a) culturing in a suitable culture medium a cell transformed with a DNA sequence comprising the nucleotide sequence of FIG. 3 or a fragment thereof which encodes a biologically active peptide capable of inducing bone and/or cartilage formation in the Rosen-modified Sampath-Reddi assay; and (b) recovering from said culture medium a protein having the amino acid set forth in FIG. 3 or said biologically active peptide.

8. The composition of claim 8 wherein said host cells are mammalian.

9. The composition of claim 8 wherein said host cells are CHO cells.

10. A composition of claim 8 further comprising a pharmaceutically acceptable matrix.

11. The composition of claim 8 wherein said matrix comprises a material from the group consisting of hydroxyapatite, collagen, polylactic acid and tricalcium phosphate.

12. The composition of claim 8 wherein said protein recovered from the culture medium comprises amino acid #412 to #513 of FIG. 3.

13. The composition of claim 8 wherein said protein recovered from the medium comprises amino acid #388 to #513 of FIG. 3.

14. The composition of claim 8 wherein said protein recovered from the medium comprises amino acid #382 to #513 of FIG. 3.

* * * * *

UNITED STATES PATENT AND TRADEMARK OFFICE
CERTIFICATE OF CORRECTION

PATENT NO.    : 5,459,047
DATED         : October 17, 1995
INVENTOR(S)   : John Wozney et al.

It is certified that error appears in the above-identified patent and that said Letters Patent is hereby corrected as shown below:

Column 30,
Lines 38, 41, 44 and 48, "claim 2" should read -- claim 1 --;
Line 50, "claim 6" should read -- claim 5 --;
Line 66, "claim 8" should read -- claim 7 --;

Column 31,
Lines 1, 3, 5 and 8, "claim 8" should read -- claim 7 --;

Column 32,
Lines 2 and 5, "claim 8" should read -- claim 7 --;

Signed and Sealed this

Fifth Day of August, 2003

JAMES E. ROGAN
*Director of the United States Patent and Trademark Office*